US012673959B2

(12) United States Patent
Lee et al.

(10) Patent No.: US 12,673,959 B2
(45) Date of Patent: Jul. 7, 2026

(54) POLYSUBSTITUTED IMIDAZOLO[4,5-C][1,2]THIAZINE DERIVATIVE AND USE THEREOF

(71) Applicant: KYUNGPOOK NATIONAL UNIVERSITY INDUSTRY-ACADEMIC COOPERATION FOUNDATION, Daegu (KR)

(72) Inventors: Taeho Lee, Daegu (KR); Jong-Sup Bae, Daegu (KR); Sangkyu Lee, Daegu (KR); Hyun Chae Sim, Daegu (KR); Ji Min Moon, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 539 days.

(21) Appl. No.: 18/268,980

(22) PCT Filed: Dec. 6, 2021

(86) PCT No.: PCT/KR2021/018368
§ 371 (c)(1),
(2) Date: Jun. 22, 2023

(87) PCT Pub. No.: WO2022/139249
PCT Pub. Date: Jun. 30, 2022

(65) Prior Publication Data

US 2024/0101574 A1 Mar. 28, 2024

(30) Foreign Application Priority Data

Dec. 23, 2020 (KR) ........................ 10-2020-0182035

(51) Int. Cl.
*C07D 513/04* (2006.01)
*A61P 31/00* (2006.01)

(52) U.S. Cl.
CPC ............ *C07D 513/04* (2013.01); *A61P 31/00* (2018.01)

(58) Field of Classification Search
CPC ............................... C07D 513/04; A61P 31/00
See application file for complete search history.

(56) References Cited

FOREIGN PATENT DOCUMENTS

ES 459524 A1 4/1978

OTHER PUBLICATIONS

International Search Report for PCT/KR2021/018368 mailed Mar. 16, 2022 from Korean Intellectual Property Office.

Martinez, A. et al., "Imidazothiadiazine Dioxides: Synthesis and Antiviral Activity", Bioorganic & Medicinal Chemistry, vol. 7, Issue 8, Aug. 1999, pp. 1617-1623.

Abdel-W Ahab, B. F. et al., "Synthetic routes to imidazothiadiazines", Phosphoms, sulfur, and silicon and the related elements, 2015, vol. 190, No. 11, pp. 1781-1790.

T Aflan, E. et al. "Novel imidazo[2,1-b][1,3,4]thiadiazole (ITD) hybrid compounds: Design, synthesis, efficient antibacterial activity and antioxidant effects", Bioorganic chemistry, 2019, vol. 89, 102998, (inner pp. 1-10).

Alwan, W. S. et al., "Novel imidazo[2,1-b ]-1,3,4-thiadiazoles as promising antifungal agents against clinical isolate of Cryptococcus neoformans" European journal of medicinal chemistry, 2015, vol. 95, pp. 514-525.

Chih-Hua Tseng et al., "Furo[30,20:3,4]naphtho[1,2-d]imidazole derivatives as potential inhibitors of inflammatory factors in sepsis", Bioorganic & medicinal chemistry, vol. 17, Issue 18, Sep. 15, 2009, pp. 6773-6779.

Huan Yang et al., "A critical cysteine is required for HMGB1 binding to Toll-like receptor 4 and activation of macrophage cytokine release", Proceedings of the National Academy of Sciences, Jun. 29, 2010, vol. 107, No. 26, p. 11942-11947.

Mitchell P Fink, "Bench-to-bedside review: High-mobility group box 1 and critical illness", Crit Care, 2007, vol. 11, No. 5, pp. 1-8.

Hideyuki Yanai et al., "Suppression of immune responses by nonimmunogenic oligodeoxynucleotides with high affinity for high-mobility group box proteins (HMGBs)", Proceedings of the National Academy of Sciences, Jun. 27, 2011, vol. 108, No. 28, pp. 11542-11547.

Jong-Sup Bae et al., "Activated protein C inhibits high mobility group box 1 signaling in endothelial cells", Blood, Oct. 6, 2011, vol. 118, No. 14, pp. 3952-3959.

Osamu Hori et al., "The Receptor for Advanced Glycation End Products (RAGE) is a Cellular Binding Site for Amphoterin", The Journal of Biological Chemistry, vol. 270, No. 43, Issue of Oct. 27, 1995, pp. 25752-25761.

Jong Sung Park et al., "Involvement of Toll-like Receptors 2 and 4 in Cellular Activation by High Mobility Group Box 1 Protein", The Journal of Biological Chemistry, vol. 279, No. 9, Issue of Feb. 27, 2004, pp. 7370-7377.

H. Wang et al., "Extracellular role of HMGB1 in inflammation and sepsis", Journal of Internal Medicine, vol. 255, Issue 3, Mar. 2004, pp. 320-331.

(Continued)

*Primary Examiner* — Kamal A Saeed
(74) *Attorney, Agent, or Firm* — Revolution IP, PLLC

(57) ABSTRACT

The present invention relates to a polysubstituted imidazolo[4,5-c][1,2]thiazine derivative and a use of an agent comprising same as an active agent, which is useful for infectious diseases associated with vascular inflammation caused by HMGB1 protein activity. It has been found that the polysubstituted imidazolo[4,5-c][1,2]thiazine derivative of the present invention increases the sepsis survival rate as a result of searching for antiseptic effects through CLP-induced sepsis animal experiments. Accordingly, the agent comprising the polysubstituted imidazolo[4,5-c][1,2]thiazine derivative or a pharmaceutically acceptable salt thereof as an active agent may be advantageously used as a therapeutic agent for infectious diseases and vascular inflammatory diseases including sepsis caused by HMGB1 protein activity.

8 Claims, 1 Drawing Sheet

(56) References Cited

OTHER PUBLICATIONS

Hong Wang et al., "Cholinergic agonists inhibit HMGB1 release and improve survival in experimental sepsis", Nature medicine, 2004, vol. 10 (11), p. 1216-1221.
Runkuan Yang et al., "Anti-HMGB1 Neutralizing Antibody Ameliorates Gut Barrier Dysfunction and Improves Survival after Hemorrhagic Shock", Molecular Medicine, 2006, vol. 12, pp. 105-114.
Sebastien Gibot et al., "High-mobility group box 1 protein plasma concentrations during septic shock", Intensive Care Medicine, 2007, vol. 33, pp. 1347-1353.
Jonas Sunden-Cullberg et al., "Persistent elevation of high mobility group box-1 protein (HMGB1) in patients with severe sepsis and septic shock", Crit Care Med, 2005, vol. 33, No. 3, pp. 564-573.

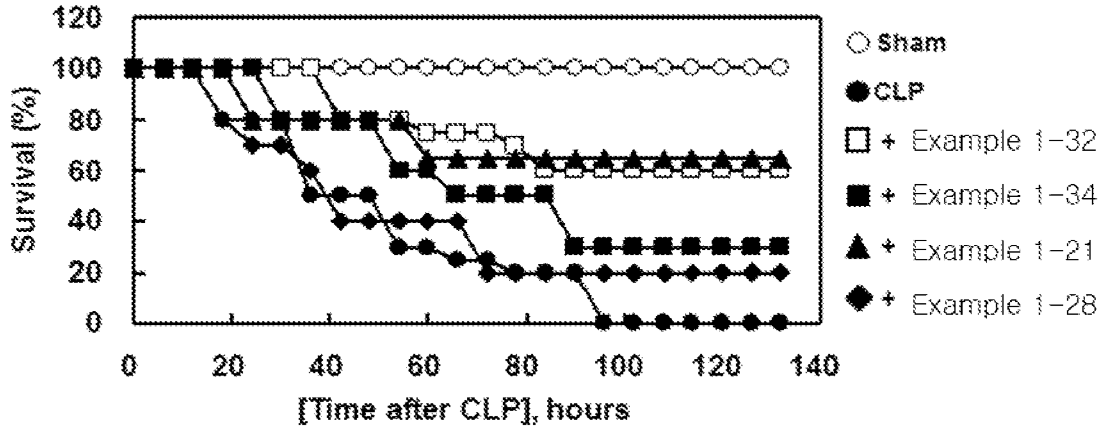
120
100
80
60
40
20
0
Survival (%)
0
20
40
60
80
100
120
140
[Time after CLP], hours
Sham
CLP
+ Example 1-32
+ Example 1-34
+ Example 1-21
+ Example 1-28
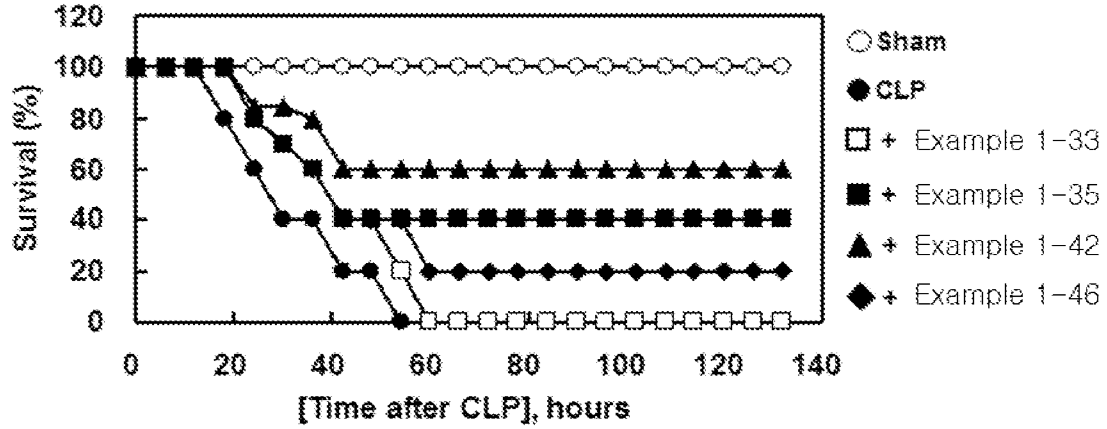
120
100
80
60
40
20
0
Survival (%)
0
20
40
60
80
100
120
140
[Time after CLP], hours
Sham
CLP
+ Example 1-33
+ Example 1-35
+ Example 1-42
+ Example 1-46

POLYSUBSTITUTED IMIDAZOLO[4,5-C][1,2]THIAZINE DERIVATIVE AND USE THEREOF

CROSS REFERENCE TO PRIOR APPLICATIONS

This application is the 35 U.S.C. 371 national stage of international application PCT/KR2021/018368 filed on Dec. 6, 2021 which claims priority to Korean Patent Application No. 10-2020-0182035 filed on Dec. 23, 2020. The entire contents of each of the above-identified applications are hereby incorporated by reference.

TECHNICAL FIELD

The present disclosure relates to a polysubstituted imidazolo[4,5-c][1,2]thiazine derivative and a use thereof. More specifically, as a novel compound exhibiting inhibitory activity in various inflammatory responses mediated by HMGB1 protein, the present disclosure provides a polysubstituted imidazolo[4,5-c][1,2]thiazine derivative and a pharmaceutically acceptable salt thereof, and relates to a pharmaceutical composition for preventing or treating vascular inflammatory diseases and infectious diseases including the same as an active ingredient.

BACKGROUND ART

Sepsis, a systemic infection caused by the leakage of bacteria into the blood, is a deadly disease that kills more than 225,000 people every year in the United States alone. Although the cause of the disease is simple, sepsis involves a wide range of mechanisms of inflammatory responses. Due to complexity, Xigris has been the only therapeutic agent approved by the US FDA in 2001, over more than 20 years of research into sepsis treatments. However, since its removal from the market in October 2011 due to doubts about its efficacy, no practical therapeutic agent has been released.

First, in the 'Proceedings of the National Academy of Sciences', Tracey researchers presented that high-mobility group box 1 (HMGB1), a transcription factor, induces a cytokine response in host cells against bacterial toxins, thus initiating the study on HMGB1 as a target protein for sepsis treatment [Yang H, PNAS, 2010, 107, 11942-11947]. HMGB1 is a DNA-binding protein known to induce inflammation [Fink M P, Critical care, 2007, 11:229]. HMGB1 is released when apoptosis or necrosis occurs in immune or non-immune cells [Anderson U, Annu. Rev. immunol., 2011, 29, 139-162]. HMGB1 released into the blood increases permeability of vascular endothelial cells, leading to induction of adhesion and migration of immune cells to cause sepsis [Bae J S, Blood, 2011, 118, 3952-3959]. In macrophages and vascular endothelial cells, HMGB1 binds to toll like receptor-2, 4 (TLR-2, 4) or receptor for the advanced glycation endproducts (RAGE) to release TNF-alpha and IL-6 and activates NF-kB and ERK-1/2 to cause severe vascular inflammation [Hon O, J. Biol. Chem., 270, 25752-25761, Park J S, J. Biol. Chem., 2004, 279, 7370-7377].

Using a mouse model of cecal ligation and puncture (CLP) surgery, which is most associated with sepsis, it was found that serum HMGB1 levels increased significantly at 18 hours after CLP surgery, and clinical symptoms of sepsis progressed thereby [Wang H, J. Internal Med., 2004, 255, 320-331]. The approach was surprising in that it was the first cytokine treatment that has greatly increased survival upon administration of antibodies against HMGB1 at 24 hours and showed effectiveness when administration was performed at 8 hours after CLP treatment [Wang H, Nat. Med. 2004, 10, 1216-1221]. Thus, in animals treated with HMGB1 inhibitors, organ damage was prevented and a protective action against lethality was maintained [Wang H, Nat. Med. 2004, 10, 1216-1221]. Clinically, studies have reported that HMGB1 is released out of cells and present in plasma even in patients with trauma or sepsis [Yang R, Molecular Medicine, 2006, 12, 105-114]. Most patients with sepsis or septic shock were found to have increased HMGB1 in plasma within one week of diagnosis, and organ damage due to systemic inflammation was observed [Gibot S, Intensive Care Med, 2007, 33, 1347-1353, Sunden-Cullberg J, Crit. Care Med., 2005, 33, 564-573]. Based on these findings, regulation of HMGB1 protein activity may be used as a treatment method for vascular inflammatory diseases and infectious diseases, including sepsis.

Accordingly, as a result of searching for a novel compound that is applicable as a therapeutic agent for vascular inflammatory diseases, the present inventors completed the present disclosure by observing excellent survival rate on sepsis, as a result of designing and synthesizing the polysubstituted imidazolo[4,5-c][1,2]thiazine derivative compound with an idea that no reports exist until now that the derivative shows an inhibitory effect on HMGB1 protein activity and conducting CLP-induced sepsis animal experiments using the prepared polysubstituted imidazolo[4,5-c][1,2]thiazine derivative compound.

DISCLOSURE OF THE INVENTION

Technical Goals

An object of the present disclosure is to provide a polysubstituted imidazolo[4,5-c][1,2]thiazine derivative compound and a pharmaceutically acceptable salt thereof using an organic synthesis technique.

Another object of the present disclosure is to provide a composition for preventing or treating vascular inflammatory diseases and infectious diseases using an inhibitory effect on HMGB1 protein activity, including a polysubstituted imidazolo[4,5-c][1,2]thiazine derivative and a pharmaceutically acceptable salt as active ingredients.

However, the technical tasks to be accomplished by the present disclosure are not limited to those above-mentioned, and other tasks not mentioned may be clearly understood by those skilled in the art from the following description.

Technical Solutions

In order to achieve the purposes of the present disclosure as described above, the present disclosure provides a polysubstituted imidazolo[4,5-c][1,2]thiazine derivative represented by the following Chemical Formula 1, a pharmaceutically acceptable salt thereof, or a stereoisomer thereof.

[Chemical Formula 1]

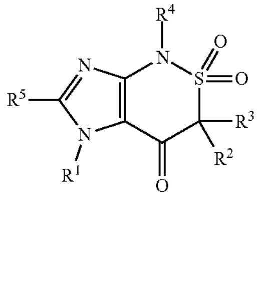

In the Chemical Formula 1, $R^1$ is hydrogen, a linear, branched, or cyclic $C_1$~$C_{10}$ alkyl group; a phenyl group or $R^6$-substituted phenyl group; a benzyl group or $R^6$-substituted benzyl group; or a $R^6$-substituted or unsubstituted aromatic group, wherein the aromatic group represents a furanyl group, a thiophenyl group, a pyridinyl group, a piperazinyl group, a pyridazinyl group, a naphthyl group, a quinolinyl group, or an isoquinolinyl group; and the $R^6$ is 1 to 3 substituents selected from the group consisting of a hydrogen atom; a halogen atom; a hydroxy group; a cyano group; a nitro group; an amino group or amino group in which 1 to 2 linear, branched, or cyclic $C_1$~$C_{10}$ alkyl groups are substituted; a linear, branched, or cyclic $C_1$~$C_{10}$ alkyl group; a $C_1$~$C_{10}$ alkoxy group; a $C_1$~$C_{10}$ haloalkoxy group; a $C_1$~$C_{10}$ haloalkyl group; and an alkoxy group including a substituted or unsubstituted aromatic ring, $R^2$ and $R^3$ are independently substituted hydrogen, a linear, branched, or cyclic $C_1$~$C_{10}$ alkyl group, a cyclic $C_1$~$C_{10}$ alkyl group including a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, $R^4$ is hydrogen, a linear, branched, or cyclic $C_1$~$C_6$ alkyl group, a cyclic $C_1$~$C_6$ alkyl group including a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, and $R^5$ represents one or more linear, branched, or cyclic $C_1$~$C_{10}$ alkyl groups, $C_1$~$C_{10}$ aryl groups, $C_1$~$C_{10}$ heteroaryl groups or substituted heteroaryl groups, amino groups substituted with $C_1$~$C_{10}$ aryl alkyl groups or $C_1$~$C_{10}$ heteroaryl alkyl groups, thio groups or phenyl groups substituted with $C_1$~$C_{10}$ aryl alkyl groups or $C_1$~$C_{10}$ heteroaryl alkyl groups, substituted phenyl groups, benzyl groups, substituted benzyl groups, linear, branched, or cyclic $C_1$~$C_{10}$ alkyl groups, or amines with piperazine

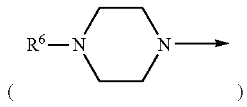

substituted with phenyl, heteroarylamide groups, wherein, in the $R^1$, $R^2$, $R^3$, and $R^4$, the substituted phenyl group, the substituted benzyl group, or the substituted $C_1$~$C_{10}$ heteroaryl group represents 1 to 4 substitutions of any one substituent selected from the group consisting of halogen atoms, nitro groups, $C_1$~$C_{10}$ alkyl groups, $C_1$~$C_{10}$ alkoxy groups, $C_1$~$C_{10}$ haloalkyl groups, and $C_1$~$C_{10}$ haloalkoxy groups.

As an example embodiment of the present disclosure, the polysubstituted imidazolo[4,5-c][1,2]thiazine derivative is any one selected from the group consisting of 1-benzyl-3,5-diphenyl-6-(propylthio)-3,5-dihydroimidazo[4,5-c][1,2]thiazine-4(1H)-one 2,2-dioxide, 1-benzyl-6-(benzylamino)-3,5-diphenyl-3,5-dihydroimidazo[4,5-c][1,2]thiazine-4(1H)-one 2,2-dioxide, 1-benzyl-6-(methylthio)-5-phenyl-3,5-dihydroimidazo[4,5-c][1,2]thiazine-4(1H)-one 2,2-dioxide, 1-benzyl-5-phenyl-6-(propylthio)-3,5-dihydroimidazo[4,5-c][1,2]thiazine-4(1H)-one 2,2-dioxide, 1-benzyl-6-(butylamino)-3,5-diphenyl-3,5-dihydroimidazo[4,5-c][1,2]thiazine-4(1H)-one 2,2-dioxide, 1-benzyl-6-(butylamino)-5-phenyl-3,5-dihydroimidazo[4,5-c][1,2]thiazine-4(1H)-one 2,2-dioxide, 1-ethyl-6-(methylsulfonyl)-3,5-diphenyl-3,5-dihydroimidazo[4,5-c][1,2]thiazine-4(1H)-one 2,2-dioxide, 1-benzyl-3-ethyl-6-(methylthio)-5-phenyl-3,5-dihydroimidazo[4,5-c][1,2]thiazine-4(1H)-one 2,2-dioxide, 1-benzyl-6-(methylthio)-3,5-diphenyl-3,5-dihydroimidazo[4,5-c][1,2]thiazine-4(1H)-one 2,2-dioxide, 1-benzyl-6-(methylsulfonyl)-3,5-diphenyl-3,5-dihydroimidazo[4,5-c][1,2]thiazine-4(1H)-one 2,2-dioxide, 1-ethyl-3,5-diphenyl-6-(phenylthio)-3,5-dihydroimidazo[4,5-c][1,2]thiazine-4(1H)-one 2,2-dioxide, 1-ethyl-3,5-diphenyl-6-(propylthio)-3,5-dihydroimidazo[4,5-c][1,2]thiazine-4(1H)-one 2,2-dioxide, 6-(butylamino)-1-ethyl-3,5-diphenyl-3,5-dihydroimidazo[4,5-c][1,2]thiazine-4(1H)-one 2,2-dioxide, 6-(benzylamino)-1-ethyl-3,5-diphenyl-3,5-dihydroimidazo[4,5-c][1,2]thiazine-4(1H)-one 2,2-dioxide, 1-benzyl-3,5-diphenyl-6-(phenylthio)-3,5-dihydroimidazo[4,5-c][1,2]thiazine-4(1H)-one 2,2-dioxide, 1-benzyl-3-(4-chlorophenyl)-5-phenyl-6-(propylthio)-3,5-dihydroimidazo[4,5-c][1,2]thiazine-4(1H)-one 2,2-dioxide, 1-benzyl-3-(4-chlorophenyl)-5-phenyl-6-(phenylthio)-3,5-dihydroimidazo[4,5-c][1,2]thiazine-4(1H)-one 2,2-dioxide, 1-benzyl-6-(butylamino)-3-(4-chlorophenyl)-5-phenyl-3,5-dihydroimidazo[4,5-c][1,2]thiazine-4(1H)-one 2,2-dioxide, 1-benzyl-6-(benzylamino)-3-(4-chlorophenyl)-5-phenyl-3,5-dihydroimidazo[4,5-c][1,2]thiazine-4(1H)-one 2,2-dioxide, 3-(4-chlorophenyl)-1-ethyl-5-phenyl-6-(propylthio)-3,5-dihydroimidazo[4,5-c][1,2]thiazine-4(1H)-one 2,2-dioxide, 3-(4-chlorophenyl)-1-ethyl-5-phenyl-6-(phenylthio)-3,5-dihydroimidazo[4,5-c][1,2]thiazine-4(1H)-one 2,2-dioxide, 6-(butylamino)-3-(4-chlorophenyl)-1-ethyl-5-phenyl-3,5-dihydroimidazo[4,5-c][1,2]thiazine-4(1H)-one 2,2-dioxide, 6-(benzylamino)-3-(4-chorophenyl)-1-ethyl-5-phenyl-3,5-dihydroimidazo[4,5-c][1,2]thiazine-4(1H)-one 2,2-dioxide, 1-benzyl-3-(4-chlorophenyl)-3-methyl-5-phenyl-6-(propylthio)-3,5-dihydroimidazo[4,5-c][1,2]thiazine-4(1H)-one 2,2-dioxide, 1-benzyl-5-methyl-3-phenyl-6-(propylthio)-3,5-dihydroimidazo[4,5-c][1,2]thiazine-4(1H)-one 2,2-dioxide, 1-benzyl-5-methyl-3-phenyl-6-(phenylthio)-3,5-dihydroimidazo[4,5-c][1,2]thiazine-4(1H)-one 2,2-dioxide, 1-benzyl-6-(butylamino)-5-methyl-3-phenyl-3,5-dihydroimidazo[4,5-c][1,2]thiazine-4(1H)-one 2,2-dioxide, 1-benzyl-6-(butylamino)-5-methyl-3-phenyl-3,5-dihydroimidazo[4,5-c][1,2]thiazine-4(1H)-one 2,2-dioxide, 1-ethyl-5-methyl-3-phenyl-6-(propylthio)-3,5-dihydroimidazo[4,5-c][1,2]thiazine-4(1H)-one 2,2-dioxide, 1-ethyl-5-methyl-3-phenyl-6-(phenylthio)-3,5-dihydroimidazo[4,5-c][1,2]thiazine-4(1H)-one 2,2-dioxide, 6-(butylamino)-1-ethyl-5-methyl-3-phenyl-3,5-dihydroimidazo[4,5-c][1,2]thiazine-4(1H)-one 2,2-dioxide, 6-(benzylamino)-1-ethyl-5-methyl-3-phenyl-3,5-dihydroimidazo[4,5-c][1,2]thiazine-4(1H)-one 2,2-dioxide, 1-benzyl-3-(4-chlorophenyl)-5-methyl-6-(propylthio)-3,5-dihydroimidazo[4,5-c][1,2]thiazine-4(1H)-one 2,2-dioxide, 1-benzyl-3-(4-chlorophenyl)-5-methyl-6-(phenylthio)-3,5-dihydroimidazo[4,5-c][1,2]thiazine-4(1H)-one 2,2-dioxide, 1-benzyl-6-(butylamino)-3-(4-chlorophenyl)-5-methyl-3,5-dihydroimidazo[4,5-c][1,2]thiazine-4(1H)-one 2,2-dioxide, 1-benzyl-6-(benzylamino)-3-(4-chlorophenyl)-5-methyl-3,5-dihydroimidazo[4,5-c][1,2]thiazine-4(1H)-one 2,2-dioxide, 3-(4-chlorophenyl)-1-ethyl-5-methyl-6-(propylthio)-3,5-dihydroimidazo[4,5-c][1,2]thiazine-4(1H)-one 2,2-dioxide, 3-(4-chlorophenyl)-1-ethyl-5-methyl-6-(phenylthio)-3,5-dihydroimidazo[4,5-c][1,2]thiazine-4(1H)-one 2,2-dioxide, 6-(butylamino)-3-(4-chlorophenyl)-1-ethyl-5-methyl-3,5-dihydroimidazo[4,5-c][1,2]thiazine-4

(1H)-one 2,2-dioxide, 6-(benzylamino)-3-(4-chlorophenyl)-1-ethyl-5-methyl-3,5-dihydroimidazo[4,5-c][1,2]thiazine-4(1H)-one 2,2-dioxide, 1-benzyl-3-(4-chlorophenyl)-5-methyl-6-(pyrrolidin-1-yl)-3,5-dihydroimidazo[4,5-c][1,2]thiazine-4(1H)-one 2,2-dioxide, 3-(4-chlorophenyl)-1-ethyl-5-methyl-6-(pyrrolidin-1-yl)-3,5-dihydroimidazo[4,5-c][1,2]thiazine-4(1H)-one 2,2-dioxide, 1-benzyl-6-morpholino-3,5-diphenyl-3,5-dihydroimidazo[4,5-c][1,2]thiazine-4(1H)-one 2,2-dioxide, 1-ethyl-3,3-dimethyl-6-(methylthio)-5-phenyl-3,5-dihydroimidazo[4,5-c][1,2]thiazine-4(1H)-one 2,2-dioxide, 1-ethyl-3-methyl-6-(methylthio)-5-phenyl-3,5-dihydroimidazo[4,5-c][1,2]thiazine-4(1H)-one 2,2-dioxide, 1,3-dibenzyl-6-(methylthio)-5-phenyl-3,5-dihydroimidazo[4,5-c][1,2]thiazine-4(1H)-one 2,2-dioxide, 1-benzyl-3-(4-methoxybenzyl)-6-(methylthio)-3,5-diphenyl-3,5-dihydroimidazo[4,5-c][1,2]thiazine-4(1H)-one 2,2-dioxide, 1-benzyl-5-methyl-3-phenyl-6-(phenylthio)-3,5-dihydroimidazo[4,5-c][1,2]thiazine-4(1H)-one 2,2-dioxide, 1-benzyl-6-(benzylamino)-5-methyl-3-phenyl-3,5-dihydroimidazo[4,5-c][1,2]thiazine-4(1H)-one 2,2-dioxide, 1,5-dimethyl-3-phenyl-6-(propylthio)-3,5-dihydroimidazo[4,5-c][1,2]thiazine-4(1H)-one 2,2-dioxide, 1,5-dimethyl-3-phenyl-6-(phenylthio)-3,5-dihydroimidazo[4,5-c][1,2]thiazine-4(1H)-one 2,2-dioxide, 6-(benzylamino)-1,5-dimethyl-3-phenyl-3,5-dihydroimidazo[4,5-c][1,2]thiazine-4(1H)-one 2,2-dioxide, 1-benzyl-5-methyl-6-(methylthio)-3-phenyl-3,5-dihydroimidazo[4,5-c][1,2]thiazine-4(1H)-one 2,2-dioxide, and 1,5-dimethyl-6-(methylsulfonyl)-3-phenyl-3,5-dihydroimidazo[4,5-c][1,2]thiazine-4(1H)-one 2,2-dioxide.

The present disclosure provides a pharmaceutical composition for preventing or treating a vascular inflammatory disease and an infectious disease, including a polysubstituted imidazolo[4,5-c][1,2]thiazine derivative represented by Chemical formula 1, or a pharmaceutically acceptable salt thereof, or a stereoisomer thereof as an active ingredient.

As an example embodiment of the present disclosure, the vascular inflammatory disease and the infectious disease are sepsis.

As another example embodiment of the present disclosure, the composition inhibits the HMGB1 protein activity.

The present disclosure provides a method of treating a vascular inflammatory disease and an infectious disease, including administering the pharmaceutical composition into an individual.

The present disclosure provides a method of using the pharmaceutical composition for prevention or treatment of a vascular inflammatory disease and an infectious disease.

Advantageous Effects

The present disclosure provides a polysubstituted imidazolo[4,5-c][1,2]thiazine derivative and a pharmaceutically acceptable salt thereof, wherein, by discovering an inhibitory effect of the derivative on HMGB1 protein activity and outstanding inhibitory activities through CLP-induced sepsis animal experiments, it is anticipated to be used for prevention or treatment of vascular inflammatory diseases and infectious diseases including sepsis through the inhibitory effect of the compound on HMGB1 protein activity.

BRIEF DESCRIPTION OF DRAWINGS

FIG. 1 shows results illustrating survival rate of mice by administration of derivatives 1-21, 1-28, 1-32, 1-33, 1-34, 1-35, 1-42, and 1-46 in a CLP-induced sepsis mouse model.

BEST MODE FOR CARRYING OUT THE INVENTION

The present disclosure provides a polysubstituted imidazolo[4,5-c][1,2]thiazine derivative represented by Chemical Formula 1 and a pharmaceutically acceptable salt thereof or a stereoisomer thereof.

[Chemical Formula 1]

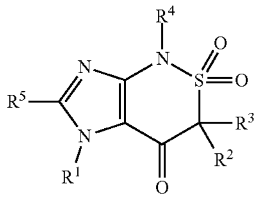

In the Chemical Formula 1, $R^1$ is hydrogen, a linear, branched, or cyclic $C_1$~$C_{10}$ alkyl group; a phenyl group or $R^6$-substituted phenyl group; a benzyl group or $R^6$-substituted benzyl group; or a $R^6$-substituted or unsubstituted aromatic group, wherein the aromatic group represents a furanyl group, a thiophenyl group, a pyridinyl group, a piperazinyl group, a pyridazinyl group, a naphthyl group, a quinolinyl group, or an isoquinolinyl group; and the $R^6$ is a 1 to 3 substituents selected from the group consisting of a hydrogen atom; a halogen atom; a hydroxy group; a cyano group; a nitro group; an amino group or amino group in which 1 to 2 linear, branched, or cyclic $C_1$~$C_{10}$ alkyl groups are substituted; a linear, branched, or cyclic $C_1$~$C_{10}$ alkyl group; a $C_1$~$C_{10}$ alkoxy group; a $C_1$~$C_{10}$ haloalkoxy group; a $C_1$~$C_{10}$ haloalkyl group; and an alkoxy group including a substituted or unsubstituted aromatic ring, $R^2$ and $R^3$ are independently substituted hydrogen, a linear, branched, or cyclic $C_1$~$C_{10}$ alkyl group, a cyclic $C_1$~$C_{10}$ alkyl group including a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted group, $R^4$ is hydrogen, a linear, branched, or cyclic $C_1$~$C_6$ alkyl group, a cyclic $C_1$~$C_6$ alkyl group including a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, and $R^5$ represents one or more linear, branched, or cyclic $C_1$~$C_{10}$ alkyl groups, $C_1$~$C_{10}$ aryl groups, $C_1$~$C_{10}$ heteroaryl groups or substituted heteroaryl groups, amino groups substituted with $C_1$~$C_{10}$ aryl alkyl groups or $C_1$~$C_{10}$ heteroaryl alkyl groups, thio groups or phenyl groups substituted with $C_1$~$C_{10}$ aryl alkyl groups or $C_1$~$C_{10}$ heteroaryl alkyl groups, substituted phenyl groups, benzyl groups, substituted benzyl groups, linear, branched, or cyclic $C_1$~$C_{10}$ alkyl groups, or amines with piperazine

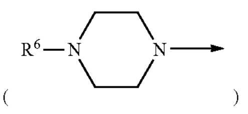

substituted with phenyl, heteroarylamide groups, wherein, in the $R^1$, $R^2$, $R^3$, and $R^4$, the substituted phenyl group, the substituted benzyl group, or the substituted $C_1$~$C_{10}$ heteroaryl group represents 1 to 4 substitutions of any one substituent selected from the group consisting of halogen atoms, nitro groups, $C_1$~$C_{10}$ alkyl groups, $C_1$~$C_{10}$ alkoxy groups, $C_1$~$C_{10}$ haloalkyl groups, and $C_1$~$C_{10}$ haloalkoxy groups.

In the polysubstituted imidazolo[4,5-c][1,2]thiazine derivative compound represented by Chemical Formula 1 according to the present disclosure, preferable description is as follows.

$R^1$ is hydrogen, a linear, branched, or cyclic $C_1$~$C_7$ alkyl group; a phenyl group or $R^6$-substituted phenyl group; a benzyl group or $R^6$-substituted benzyl group; or a $R^6$-substituted or unsubstituted aromatic group, wherein the aromatic group represents a furanyl group, a thiophenyl group, a pyridinyl group, a piperazinyl group, a pyridazinyl group, a naphthyl group, a quinolinyl group, or an isoquinolinyl group; and the $R^6$ is a 1 to 3 substituents selected from the group consisting of a hydrogen atom; a halogen atom; a hydroxy group; a cyano group; a nitro group; an amino group or amino group in which 1 to 2 linear, branched, or cyclic $C_1$~$C_5$ alkyl groups are substituted; a linear, branched, or cyclic $C_1$~$C_5$ alkyl group; a $C_1$~$C_5$ alkoxy group; a $C_1$~$C_5$ haloalkoxy group; a $C_1$~$C_5$ haloalkyl group; and an alkoxy group including a substituted or unsubstituted aromatic ring, $R^2$ and $R^3$ are independently substituted hydrogen, a linear, branched, or cyclic $C_1$~$C_7$ alkyl group, a cyclic $C_1$~$C_7$ alkyl group including a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, $R^4$ is hydrogen, a linear, branched, or cyclic $C_1$~$C_4$ alkyl group, a cyclic $C_1$-$C_4$ alkyl group including a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, and $R^5$ represents one or more linear, branched, or cyclic $C_1$~$C_7$ alkyl groups, $C_1$~$C_7$ aryl groups, $C_1$~$C_7$ heteroaryl groups or substituted heteroaryl groups, amino groups substituted with $C_1$~$C_7$ aryl alkyl groups or $C_1$~$C_7$ heteroaryl alkyl groups, thio groups or phenyl groups substituted with $C_1$~$C_7$ aryl alkyl groups or $C_1$~$C_7$ heteroaryl alkyl groups, substituted phenyl groups, benzyl groups, substituted benzyl groups, linear, branched, or cyclic $C_1$~$C_7$ alkyl groups, or amines with piperazine

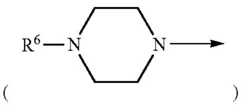

substituted with phenyl, heteroarylamide groups, wherein, in the $R^1$, $R^2$, $R^3$, and $R^4$, the substituted phenyl group, the substituted benzyl group, or the substituted $C_1$~$C_7$ heteroaryl group represents 1 to 3 substitutions of any one substituent selected from the group consisting of halogen atoms, nitro groups, $C_1$~$C_7$ alkyl groups, $C_1$~$C_7$ alkoxy groups, $C_1$~$C_7$ haloalkyl groups, and $C_1$~$C_7$ haloalkoxy groups.

In the polysubstituted imidazolo[4,5-c][1,2]thiazine derivative compound represented by Chemical Formula 1 according to the present disclosure, preferable description is as follows.

In the polysubstituted imidazolo[4,5-c][1,2]thiazine derivative compound, $R^1$ is hydrogen, a linear, branched, or cyclic $C_1$~$C_7$ alkyl group; a phenyl group or $R^6$-substituted phenyl group; or a $R^6$-substituted or unsubstituted aromatic group, wherein the aromatic group represents a furanyl group, a thiophenyl group, a pyridinyl group, a piperazinyl group, a pyridazinyl group, a quinolinyl group, or an isoquinolinyl group; and the $R^5$ is a 1 to 3 substituents selected from the group consisting of a hydrogen atom; a halogen atom; a hydroxy group; a cyano group; a nitro group; an amino group or amino group in which 1 to 2 linear, branched, or cyclic $C_1$~$C_5$ alkyl groups are substituted; a $C_1$~$C_5$ alkoxy group; and an alkoxy group including a substituted or unsubstituted aromatic ring, $R^2$ and $R^3$ are independently substituted hydrogen, a linear, branched, or cyclic $C_1$~$C_5$ alkyl group, a cyclic $C_1$~$C_5$ alkyl group including a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, $R^4$ is hydrogen, a linear, branched, or cyclic $C_1$~$C_3$ alkyl group, a cyclic $C_1$~$C_3$ alkyl group including a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, and $R^5$ represents one or more linear, branched, or cyclic $C_1$~$C_7$ alkyl groups, $C_1$~$C_3$ aryl groups, $C_1$~$C_3$ heteroaryl groups or substituted heteroaryl groups, amino groups substituted with $C_1$~$C_3$ aryl alkyl groups or $C_1$~$C_3$ heteroaryl alkyl groups, thio groups or phenyl groups substituted with $C_1$~$C_3$ aryl alkyl groups or $C_1$~$C_3$ heteroaryl alkyl groups, substituted phenyl groups, benzyl groups, or substituted benzyl groups, wherein, in the $R^1$, $R^2$, $R^3$, and $R^4$, in the substituted phenyl groups, substituted benzyl groups, or substituted heteroaryl groups, the substituent represents 1 to 3 substitutions of any one substituent selected from the group consisting of $C_1$~$C_5$ alkyl groups, $C_1$~$C_5$ alkoxy groups, $C_1$~$C_5$ haloalkoxy groups, halogen groups, nitro groups, and amine groups.

In addition, in the polysubstituted imidazolo[4,5-c][1,2] thiazine derivative compound represented by Chemical Formula 1 according to the present disclosure, preferable description is as follows.

1-benzyl-3,5-diphenyl-6-(propylthio)-3,5-dihydroimidazo[4,5-c][1,2]thiazine-4(1H)-one 2,2-diooxide, 1-benzyl-6-(benzylamino)-3,5-diphenyl-3,5-dihydroimidazo[4,5-c][1,2]thiazine-4(1H)-one 2,2-diooxide, 1-benzyl-6-(methylthio)-5-phenyl-3,5-dihydroimidazo[4,5-c][1,2]thiazine-4(1H)-one 2,2-diooxide, 1-benzyl-5-phenyl-6-(propylthio)-3,5-dihydroimidazo[4,5-c][1,2]thiazine-4(1H)-one 2,2-dioxide, 1-benzyl-6-(butylamino)-3,5-diphenyl-3,5-dihydroimidazo[4,5-c][1,2]thiazine-4(1H)-one 2,2-dioxide, 1-benzyl-6-(butylamino)-5-phenyl-3,5-dihydroimidazo[4,5-c][1,2]thiazine-4(1H)-one 2,2-dioxide, 1-ethyl-6-(methylsulfonyl)-3,5-diphenyl-3,5-dihydroimidazo[4,5-c][1,2]thiazine-4(1H)-one 2,2-dioxide, 1-benzyl-3-ethyl-6-

(methylthio)-5-phenyl-3,5-dihydroimidazo[4,5-c][1,2]thiazine-4(1H)-one 2,2-dioxide, 1-benzyl-6-(methylthio)-3,5-diphenyl-3,5-dihydroimidazo[4,5-c][1,2]thiazine-4(1H)-one 2,2-dioxide, 1-benzyl-6-(methylsulfonyl)-3,5-diphenyl-3,5-dihydroimidazo[4,5-c][1,2]thiazine-4(1H)-one 2,2-dioxide, 1-ethyl-3,5-diphenyl-6-(phenylthio)-3,5-dihydroimidazo[4,5-c][1,2]thiazine-4(1H)-one 2,2-dioxide, 1-ethyl-3,5-diphenyl-6-(propylthio)-3,5-dihydroimidazo[4,5-c][1,2]thiazine-4(1H)-one 2,2-dioxide, 6-(butylamino)-1-ethyl-3,5-diphenyl-3,5-dihydroimidazo[4,5-c][1,2]thiazine-4(1H)-one 2,2-dioxide, 6-(benzylamino)-1-ethyl-3,5-diphenyl-3,5-dihydroimidazo[4,5-c][1,2]thiazine-4(1H)-one 2,2-dioxide, 1-benzyl-3,5-diphenyl-6-(phenylthio)-3,5-dihydroimidazo[4,5-c][1,2]thiazine-4(1H)-one 2,2-dioxide, 1-benzyl-3-(4-chlorophenyl)-5-phenyl-6-(propylthio)-3,5-dihydroimidazo[4,5-c][1,2]thiazine-4(1H)-one 2,2-dioxide, 1-benzyl-3-(4-chlorophenyl)-5-phenyl-6-(phenylthio)-3,5-dihydroimidazo[4,5-c][1,2]thiazine-4(1H)-one 2,2-dioxide, 1-benzyl-6-(butylamino)-3-(4-chlorophenyl)-5-phenyl-3,5-dihydroimidazo[4,5-c][1,2]thiazine-4(1H)-one 2,2-dioxide, 1-benzyl-6-(benzylamino)-3-(4-chlorophenyl)-5-phenyl-3,5-dihydroimidazo[4,5-c][1,2]thiazine-4(1H)-one 2,2-dioxide, 3-(4-chlorophenyl)-1-ethyl-5-phenyl-6-(propylthio)-3,5-dihydroimidazo[4,5-c][1,2]thiazine-4(1H)-one 2,2-dioxide, 3-(4-chlorophenyl)-1-ethyl-5-phenyl-6-(phenylthio)-3,5-dihydroimidazo[4,5-c][1,2]thiazine-4(1H)-one 2,2-dioxide, 6-(butylamino)-3-(4-chlorophenyl)-1-ethyl-5-phenyl-3,5-dihydroimidazo[4,5-c][1,2]thiazine-4(1H)-one 2,2-dioxide, 6-(benzylamino)-3-(4-chlorophenyl)-1-ethyl-5-phenyl-3,5-dihydroimidazo[4,5-c][1,2]thiazine-4(1H)-one 2,2-dioxide, 1-benzyl-3-(4-chlorophenyl)-3-methyl-5-phenyl-6-(propylthio)-3,5-dihydroimidazo[4,5-c][1,2]thiazine-4(1H)-one 2,2-dioxide, 1-benzyl-5-methyl-3-phenyl-6-(propylthio)-3,5-dihydroimidazo[4,5-c][1,2]thiazine-4(1H)-one 2,2-dioxide, 1-benzyl-5-methyl-3-phenyl-6-(phenylthio)-3,5-dihydroimidazo[4,5-c][1,2]thiazine-4(1H)-one 2,2-dioxide, 1-benzyl-6-(butylamino)-5-methyl-3-phenyl-3,5-dihydroimidazo[4,5-c][1,2]thiazine-4(1H)-one 2,2-dioxide, 1-benzyl-6-(butylamino)-5-methyl-3-phenyl-3,5-dihydroimidazo[4,5-c][1,2]thiazine-4(1H)-one 2,2-dioxide, 1-ethyl-5-methyl-3-phenyl-6-(propylthio)-3,5-dihydroimidazo[4,5-c][1,2]thiazine-4(1H)-one 2,2-dioxide, 1-ethyl-5-methyl-3-phenyl-6-(phenylthio)-3,5-dihydroimidazo[4,5-c][1,2]thiazine-4(1H)-one 2,2-dioxide, 6-(butylamino)-1-ethyl-5-methyl-3-phenyl-3,5-dihydroimidazo[4,5-c][1,2]thiazine-4(1H)-one 2,2-dioxide, 6-(benzylamino)-1-ethyl-5-methyl-3-phenyl-3,5-dihydroimidazo[4,5-c][1,2]thiazine-4(1H)-one 2,2-dioxide, 1-benzyl-3-(4-chlorophenyl)-5-methyl-6-(propylthio)-3,5-dihydroimidazo[4,5-c][1,2]thiazine-4(1H)-one 2,2-dioxide, 1-benzyl-3-(4-chlorophenyl)-5-methyl-6-(phenylthio)-3,5-dihydroimidazo[4,5-c][1,2]thiazine-4(1H)-one 2,2-dioxide, 1-benzyl-6-(butylamino)-3-(4-chlorophenyl)-5-methyl-3,5-dihydroimidazo[4,5-c][1,2]thiazine-4(1H)-one 2,2-dioxide, 1-benzyl-6-(benzylamino)-3-(4-chlorophenyl)-5-methyl-3,5-dihydroimidazo[4,5-c][1,2]thiazine-4(1H)-one 2,2-dioxide, 3-(4-chlorophenyl)-1-ethyl-5-methyl-6-(propylthio)-3,5-dihydroimidazo[4,5-c][1,2]thiazine-4(1H)-one 2,2-dioxide, 3-(4-chlorophenyl)-1-ethyl-5-methyl-6-(phenylthio)-3,5-dihydroimidazo[4,5-c][1,2]thiazine-4(1H)-one 2,2-dioxide, 6-(butylamino)-3-(4-chlorophenyl)-1-ethyl-5-methyl-3,5-dihydroimidazo[4,5-c][1,2]thiazine-4(1H)-one 2,2-dioxide, 6-(benzylamino)-3-(4-chlorophenyl)-1-ethyl-5-methyl-3,5-dihydroimidazo[4,5-c][1,2]thiazine-4(1H)-one 2,2-dioxide, 1-benzyl-3-(4-chlorophenyl)-5-methyl-6-(pyrrolidin-1-yl)-3,5-dihydroimidazo[4,5-c][1,2]thiazine-4(1H)-one 2,2-dioxide, 3-(4-chlorophenyl)-1-ethyl-5-methyl-6-(pyrrolidin-1-yl)-3,5-dihydroimidazo[4,5-c][1,2]thiazine-4(1H)-one 2,2-dioxide, 1-benzyl-6-morpholino-3,5-diphenyl-3,5-dihydroimidazo[4,5-c][1,2]thiazine-4(1H)-one 2,2-dioxide, 1-ethyl-3,3-dimethyl-6-(methylthio)-5-phenyl-3,5-dihydroimidazo[4,5-c][1,2]thiazine-4(1H)-one 2,2-dioxide, 1-ethyl-3-methyl-6-(methylthio)-5-phenyl-3,5-dihydroimidazo[4,5-c][1,2]thiazine-4(1H)-one 2,2-dioxide, 1,3-dibenzyl-6-(methylthio)-5-phenyl-3,5-dihydroimidazo[4,5-c][1,2]thiazine-4(1H)-one 2,2-dioxide, 1-benzyl-3-(4-methoxybenzyl)-6-(methylthio)-3,5-diphenyl-3,5-dihydroimidazo[4,5-c][1,2]thiazine-4(1H)-one 2,2-dioxide, 1-benzyl-5-methyl-3-phenyl-6-(phenylthio)-3,5-dihydroimidazo[4,5-c][1,2]thiazine-4(1H)-one 2,2-dioxide, 1-benzyl-6-(benzylamino)-5-methyl-3-phenyl-3,5-dihydroimidazo[4,5-c][1,2]thiazine-4(1H)-one 2,2-dioxide, 1,5-dimethyl-3-phenyl-6-(propylthio)-3,5-dihydroimidazo[4,5-c][1,2]thiazine-4(1H)-one 2,2-dioxide, 1,5-dimethyl-3-phenyl-6-(phenylthio)-3,5-dihydroimidazo[4,5-c][1,2]thiazine-4(1H)-one 2,2-dioxide, 6-(benzylamino)-1,5-dimethyl-3-phenyl-3,5-dihydroimidazo[4,5-c][1,2]thiazine-4(1H)-one 2,2-dioxide, 1-benzyl-5-methyl-6(methylthio)-3-phenyl-3,5-dihydroimidazo[4,5-c][1,2]thiazine-4(1H)-one 2,2-dioxide, and 1,5-dimethyl-6-(methylsulfonyl)-3-phenyl-3,5-dihydroimidazo[4,5-c][1,2]thiazine-4(1H)-one 2,2-dioxide.

The term "pharmaceutically acceptable salt thereof or a stereoisomer thereof" as used herein refers to one that may be prepared by a conventional method in the art, for example, it refers to formation of salts of acids of those that are pharmaceutically acceptable along with salts of inorganic acids such as hydrochloric acid, hydrogen bromide, sulfuric acid, sodium hydrogen sulfate, phosphoric acid, and carbonic acid or organic acids such as formic acid, acetic acid, oxalic acid, benzoic acid, citric acid, tartaric acid, gluconic acid, gentisic acid, fumaric acid, lactobionic acid, salicylic acid, or acetylsalicylic acid (aspirin), or formation of metal salts of alkali metal ions by reacting with the alkali metal ions such as sodium and potassium or formation of other types of pharmaceutically acceptable salts of ammonium ions by reacting with the ammonium ions.

According to an example embodiment of the present disclosure, the anti-inflammatory efficacy of the prepared compound was determined through the survival rate of a peritonitis-induced sepsis mouse model (Example 3). Accordingly, the polysubstituted imidazolo[4,5-c][1,2]thiazine derivative of the present disclosure, pharmaceutically acceptable salt thereof, or stereoisomer thereof may be used to prevent or treat a vascular inflammatory disease.

Thus, the present disclosure provides a pharmaceutical composition for preventing or treating a vascular inflammatory disease and an infectious disease, including a polysubstituted imidazolo[4,5-c][1,2]thiazine derivative or a pharmaceutically acceptable salt thereof, or a stereoisomer thereof as an active ingredient.

The term "prevention" as used herein refers to any action that suppresses or delays the onset of the vascular inflammatory disease by administration of the pharmaceutical composition according to the present disclosure.

The term "treatment" as used herein refers to any action that symptoms of the vascular inflammatory disease are alleviated or changed beneficially by administration of the pharmaceutical composition according to the present disclosure.

The term "individual" as used herein refers to a target in need of treatment for a disease, and more specifically, to mammals that are human or non-human such as primates, mice, rats, dogs, cats, horses, and cattle.

In the present disclosure, the vascular inflammatory disease and the infectious disease may be arteriosclerosis and vasculitis, but is not limited thereto, and preferably sepsis The pharmaceutical composition of the present disclosure includes a polysubstituted imidazolo[4,5-c][1,2]thiazine derivative compound represented by the Chemical Formula 1, a pharmaceutically acceptable salt thereof, or a stereoisomer thereof, a solvent thereof, or a hydrate thereof as an active ingredient, and, by adding conventional non-toxic pharmaceutically acceptable carriers, reinforcing agents and excipients, it is possible to formulate into preparations that are conventional in the pharmaceutical field, including oral preparations or parenteral preparations such as tablets, capsules, troches, solutions, and suspensions.

Excipients that may be used in the pharmaceutical composition of the present disclosure may include sweeteners, binders, dissolving agents, dissolving aids, humectants, emulsifiers, isotonic agents, adsorbents, disintegrants, antioxidants, preservatives, glydents, fillers, and air fresheners. Examples include lactose, dextrose, sucrose, mannitol, sorbitol, cellulose, glycine, silica, talc, stearic acid, sterin, magnesium stearate, magnesium aluminum silicate, starch, gelatin, tragacanth rubber, alginic acid, sodium alginate, methylcellulose, sodium carboxylmethylcellulose, agar, water, ethanol, polyethylene glycol, polyvinylpyrrolidone, sodium chloride, calcium chloride, orange essence, strawberry essence, and vanilla flavor.

The pharmaceutical composition according to the present disclosure is administered in a pharmaceutically effective amount. In the present disclosure, the term "pharmaceutically effective amount" refers to an amount sufficient to treat a disease at a reasonable benefit/risk ratio applicable to medical treatment, and the effective dose level may be determined by the type of disease of a patient, the severity, activity of a drug, sensitivity to the drug, duration of administration, administration route and discharge rate, the duration of treatment, elements including drugs used concomitantly, and other elements well known in the medical field. The pharmaceutical composition according to the present disclosure may be administered as an individual therapeutic agent or in combination with other therapeutic agents, administered sequentially or simultaneously with the conventional therapeutic agent, and administered in single or multiple doses. Considering all the factors above, it is important to administer an amount that may derive the maximum effect with the minimum amount without side effects, which may be easily determined by those skilled in the art.

Specifically, the effective amount of the pharmaceutical composition according to the present disclosure may vary depending on the age, sex, condition, weight of a patient, absorption degree of the active ingredient in vivo, inertness rate and excretion rate, types of diseases, and concomitant drugs, and administration may be generally performed in a dose of 0.1 mg/kg to 100 mg/kg per day, preferably 1 to 30 mg/kg, and may be performed once a day or divided into several times.

The pharmaceutical composition of the present disclosure may be administered into individuals by various routes. All administration methods that are expected may include, for example, oral, rectal or intravenous, intramuscular, subcutaneous, intrauterine dural, or cerebrovascular injection. The pharmaceutical composition of the present disclosure is determined depending on the type of a drug that is the active ingredient, along with several related factors such as the disease to be treated, the route of administration, the age, sex and weight of the patient, and the severity of the disease.

Furthermore, the pharmaceutical composition of the present disclosure may be used alone or in combination with methods involving surgery, hormone therapy, drug therapy, and biological response regulators for prevention and treatment of vascular inflammatory diseases and infectious diseases.

The present disclosure provides a method of preparing a polysubstituted imidazolo[4,5-c][1,2]thiazine derivative represented by Chemical Formula 1.

A brief description of the preparation method of the present disclosure is shown in the following Scheme 1.

[Scheme 1]

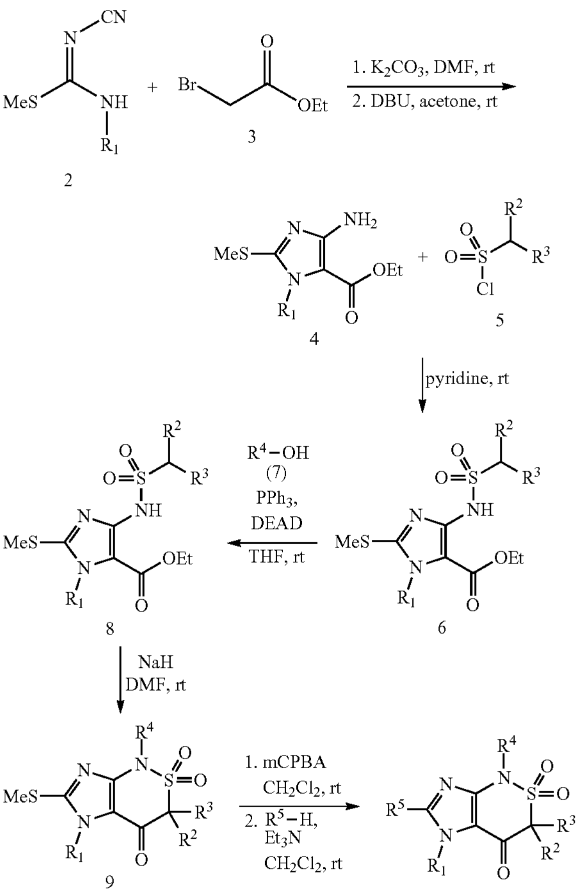

(In Scheme 1, $R^1$, $R^2$, $R^3$, $R^4$, and $R^5$ are respectively the same as defined above.)

More specifically, the preparation method includes: a first step of reacting conventionally obtainable methyl N'-cyano-N-alkyl carbamide imidothioate compound represented by Chemical Formula 2 with $R^1$ substituted with commercially available ethyl 2-bromoacetate represented by Chemical Formula 3 to synthesize ethyl 4-amino-2-(methylthio)-1-alkyl-1H-imidazole-5-carboxylate represented by Chemical Formula 4 with $R^1$ introduced and substituted;

a second step of reacting ethyl 4-amino-2-(methylthio)-1-alkyl-1H-imidazole-5-carboxylate represented by Chemical Formula 4 with $R^1$ substituted with commercially available sulfonyl chloride represented by Chemical Formula 5 with $R^2$ and $R^3$ substituted to synthesize an imidazolo[4,5-c][1,2]thiazine precursor represented by Chemical Formula 6 with $R^1$, $R^2$, and $R^3$ substituted;

a third step of synthesizing an imidazolo[4,5-c][1,2]thiazine precursor represented by Chemical Formula 8 with $R^1$, $R^2$, and $R^3$ substituted through a Mitsunobu reaction between the imidazolo[4,5-c][1,2]thiazine precursor represented by Chemical Formula 6 with $R^1$, $R^2$, and $R^3$ substituted and commercially available alcohol represented by Chemical Formula 7 with $R^4$ substituted;

a fourth step of synthesizing an imidazolo[4,5-c][1,2] thiazine precursor represented by Chemical Formula 9 with $R^1$, $R^2$, $R^3$, and $R^4$ substituted through intramolecular cyclization of the imidazolo[4,5-c][1,2]thiazine precursor represented by Chemical Formula 8 with $R^1$, $R^2$, and $R^3$ substituted; and a fifth step of carrying out, after converting a sulfide portion of the imidazolo[4,5-c][1,2]thiazine precursor represented by Chemical Formula 9 with $R^1$, $R^2$, $R^3$, and $R^4$ substituted into sulfone, a reaction with a $R^5$—H compound that may act as a nucleophile to synthesize a polysubstituted imidazolo[4,5-c][1,2]thiazine compound represented by Chemical Formula 1 with $R^1$, $R^2$, $R^3$, $R^4$, and $R^5$ introduced.

The detailed descriptions of the selection range of a reaction process, a composition of a solvent system, and reaction conditions according to the present disclosure are as follows.

In the process of the first step, the reaction to synthesize ethyl 4-amino-2-(methylthio)-1-alkyl-1H-imidazole-5-carboxylate represented by Chemical Formula 4 with $R^1$ substituted involves the use of acetone, methanol (MeOH), ethanol (EtOH), acetonitrile (MeCN), dichloromethane ($CH_2Cl_2$), dichloroethane ($ClCH_2CH_2Cl$), dioxane, tetrahydrofuran (THF), N,N-dimethylformamide (DMF), N,N-dimethyl acetamide (DMA), or dimethyl sulfoxide (DMSO) as solvents, preferably N,N-dimethylformamide (DMF) or acetone.

It is desirable to use 1 to 5 equivalents of ethyl 2-bromoacetate represented by Chemical Formula 3 used in this reaction for a methyl N'-cyano-N-alkylcarbamimidothioate compound represented by Chemical Formula 2 with $R^1$ substituted, preferably, it is economical to use in the range of 1 to 2 equivalents. In this case, potassium carbonate ($K_2CO_3$), triethylamine ($Et_3N$), sodium methoxide (NaOMe), sodium ethoxide (NaOEt), N,N-diisopropylethylamine (DIPEA), 1,8-diazabicyclo[5.4.0]undec-7-ene (DBU), and 1,5-diazabicyclo[4.3.0]non-5-ene may be used representatively as bases or reagents, preferably potassium carbonate or DBU.

In the reaction of the second step, pyridine, tetrahydrofuran, toluene, acetone, and acetonitrile are used as solvents, preferably pyridine. In this case, pyridine, potassium carbonate, triethylamine, sodium methoxide (NaOMe), sodium ethoxide (NaOEt), 1,8-diazabicyclo[5.4.0]undec-7-ene (DBU), and 1,5-diazabicyclo[4.3.0]non-5-ene may be used representatively as bases or reagents, preferably pyridine. In this case, sulfonyl chloride including the factors as defined above may be used for $R^2$ and $R^3$ substituents used. In this reaction, it is recommended to use 1 to 5 equivalents of sulfonyl chloride, preferably it is economical to use in the range of about 1.5 equivalents.

In the reaction of the third step, tetrahydrofurans, dichloromethane ($CH_2Cl_2$), toluene, acetone and acetonitrile are used as solvents, preferably tetrahydrofuran. In the case, DEAD and DIAD may be used representatively as reagents for the Mitsunobu reaction, and preferably DEAD. As an additional reagent, $PPh_3$ and $PBu_3$ may be used representatively, preferably $PPh_3$.

In this case, alcohol including the factor as defined above may be used for a $R^4$ substituent used. In this reaction, it is recommended to use 1 to 5 equivalents of alcohol, preferably it is economical to use in the range of about 1.5 equivalents.

In the reaction of the fourth step, acetone, methanol (MeOH), ethanol (EtOH), acetonitrile (MeCN), dichloromethane ($CH_2Cl_2$), dichloroethane ($ClCH_2CH_2Cl$), dioxane, tetrahydrofuran (THF), N,N-dimethylformamide (DMF), N,N-dimethylacetamide (DMA), or dimethylsulfoxide (DMSO) are used as solvents, preferably N,N-dimethylformamide (DMF) or acetone. In this case, hydrochloric acid (HCl), sulfuric acid ($H_2SO_4$), p-toluenesulfonic acid hydrate ($TsOH{\cdot}H_2O$), camphorsulfonic acid (CSA), sodium hydride (NaH), sodium methoxide (NaOMe), sodium ethoxide (NaOEt), 1,8-diazabicyclo[5.4.0]undec-7-ene (DBU), and 1,5-diazabicyclo[4.3.0]non-5-ene may be used representatively as acids or reagents, preferably sodium hydride.

In the process of the fifth step, the reaction to oxidize sulfide to sulfone involves the use of dichloromethane ($CH_2Cl_2$), acetonitrile (MeCN), dichloroethane ($ClCH_2CH_2Cl$), dioxane, or tetrahydrofuran (THF) as solvents, preferably dichloromethane. For an oxidizer used in this reaction, it is recommended to use in the range of 2 to 5 equivalents for the compound represented by the Chemical Formula 5, preferably it is economical to use in the range of 2 to 3 equivalents. In this case, meta-chloroperbenzoic acid (mCPBA), hydrogen peroxide, or oxone may be used as oxidizers used, and preferably it is most effective to use meta-chloroperbenzoic acid.

In the process of the fifth step, the reaction to substitute sulfone with a nucleophile of $R^5$—H involves the use of ethanol, methanol, dichloromethane, acetonitrile, dichloroethane, dioxane, tetrahydrofuran, N,N-dimethylformamide, N,N-dimethylacetamide, dimethylsulfoxide, chloroform, or acetone as solvents, preferably dichloromethane. As bases used in this reaction, N,N-diisopropylethylamine, triethylamine, sodium methoxide, and sodium ethoxide may be used representatively, and preferably it is most effective to use triethylamine.

In addition, in the process of preparing the polysubstituted imidazolo[4,5-c][1,2]thiazine derivative compound represented by the Chemical Formula 1 according to the present disclosure, the degree of reaction progressed was observed by the TLC method in the middle of the reaction, the resulting derivative compound represented by the Chemical Formulas 1-1 to 1-52 were separated and purified, and the structures were analyzed and identified by NMR or mass spectra (see Examples 1 and 2).

Modes for Carrying Out the Invention

Hereinafter, preferred example embodiments are presented to help understanding of the present disclosure. However, the following example embodiments are only provided to help understanding of the present disclosure more easily, and the contents of the present disclosure are not limited by the following example embodiments.

Example 1. Synthesis of a Polysubstituted imidazolo[4,5-c][1,2]thiazine Derivative Compound (Chemical Formula 1-1)

Step 1: Synthesis of ethyl 4-amino-2-(methylthio)-1-phenyl-1H-imidazole-5-carboxylate

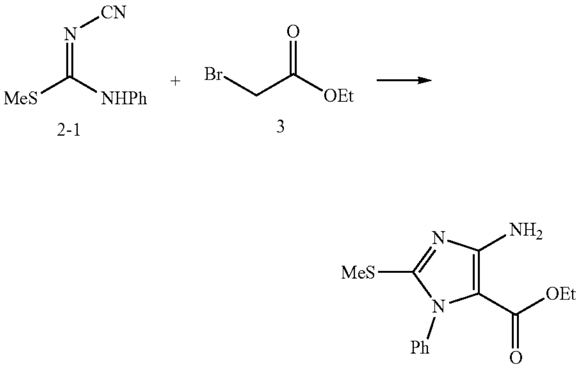

2-1 3

4-1

In a solution in which methyl N'-cyano-N-phenyl carbamimidothioate (1.50 g, 7.84 mmol) represented by Chemical Formula 2-1 was dissolved in DMF (30 mL), potassium carbonate (3.25 g, 23.5 mmol) and ethyl 2-bromoacetate (1.33 mL, 11.8 mmol) represented by Chemical Formula 3 were added and stirred at room temperature for 12 hours, the mixture was extracted with water and ethyl acetate, and then the collected organic solution was dried. The dried mixture was dissolved in acetone (50 mL), and DBU (1.79 mL, 11.8 mmol) was placed at 0° C. and stirred at room temperature for 3 hours. After the end of the reaction, the solvent was concentrated to obtain a mixture. The concentrated reaction mixture was separated and purified by column chromatography on silica gel under a mixed solvent of hexane/ethyl acetate (3/1, v/v) to obtain white solid ethyl 4-amino-2-(methylthio)-1-phenyl-1H-imidazole-5-carboxylate (1.69 g, 78% yield) represented by Chemical Formula 4-1. ($^1$NMR (500 MHz, $CDCl_3$) δ 7.45-7.43 (m, 3H), 7.26-7.24 (m, 2H), 5.01 (br s, 2H), 4.05 (q, J=7.1 Hz, 2H), 2.55 (s, 3H), 1.01 (t, J=6.5 Hz, 3H); $^{13}$C NMR (125 MHz, $CDCl_3$) δ 160.5, 155.8, 149.5, 137.0, 128.88, 128.86, 127.7, 105.3, 59.3, 14.6, 14.26; LC-MS(ESI) m/z 278 ($[M+1]^+$)).

Step 2: Synthesis of ethyl 2-(methylthio)-1-phenyl-4-(phenylmethylsulfonamido)-1H imidazole-5-carboxylate

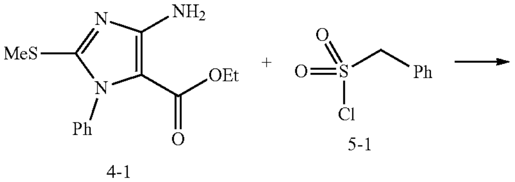

4-1 5-1

-continued

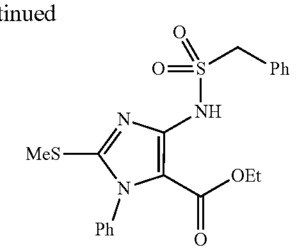

6-1

Amino imidazole ester (500 mg, 1.8 mmol) represented by Chemical Formula 4-1 was dissolved in pyridine (20 mL), and phenylmethanesulfonyl chloride (1.04 g, 5.4 mmol) represented by Chemical Formula 5-1 was added at 0° C. and stirred at room temperature for 30 minutes. After the end of the reaction, extraction was performed using water and ethyl acetate at room temperature, and the collected organic solution was dried and concentrated with anhydrous magnesium sulfate. The concentrated reaction mixture was separated and purified by column chromatography on silica gel under a mixed solvent of hexane/ethyl acetate (4/1, v/v) to obtain yellow solid ethyl 2-(methylthio)-1-phenyl-4-(phenylmethylsulfonamido)-1H imidazole-5-carboxylate (673 mg, 86% yield) represented by the Chemical Formula 6-1. ($^1$H NMR (500 MHz, $CDCl_3$) δ 7.95 (s, 1H), 7.52-7.48 (m, 3H), 7.47-7.42 (m, 2H), 7.39 (dd, J=6.6, 3.6 Hz, 3H), 7.28 (dd, J=6.5, 3.2 Hz, 2H), 4.93 (s, 2H), 4.03 (q, J=7.1 Hz, 2H), 2.68 (s, 3H), 0.97 (t, J=7.1 Hz, 3H). $^{13}$C NMR (125 MHz, $CDCl_3$) δ 159.48, 150.11, 146.47, 135.97, 130.99, 129.64, 129.22, 129.10, 129.00, 128.89, 127.63, 109.55, 60.49, 60.14, 14.87, 13.94.)

Step 3: Synthesis of ethyl 4-(N-benzyl-1-phenylmethylsulfonamido)-2-(methylthio)-1-phenyl-1H imidazole-5-carboxylate

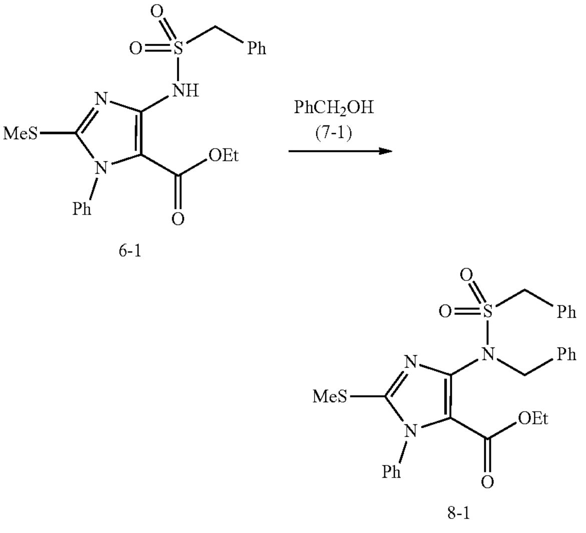

6-1

8-1

The compound (145 mg, 0.336 mmol) represented by Chemical Formula 6-1 was dissolved in THF (5 mL), and benzyl alcohol (0.1 mL, 1 mmol) represented by Chemical Formula 7-1, diethyl azodicarboxylate (DEAD, 0.16 mL, 1 mmol), and triphenylphosphine (265 mg, 1 mmol) were added and stirred at room temperature for 12 hours. After the end of the reaction, extraction was performed using water and ethyl acetate at room temperature, and the collected organic solution was dried and concentrated with anhydrous magnesium sulfate. The concentrated reaction mixture was separated and purified by column chromatography on silica gel under a mixed solvent of hexane/ethyl acetate (5/1, v/v) to obtain ethyl 4-(N-benzyl-1-phenylmethylsulfonamido)-2-(methylthio)-1-phenyl-1H imidazole-5-carboxylate (158 mg, 99% yield) represented by the Chemical Formula 8-1 in a colorless oil form. ($^1$H NMR (500 MHz, $CDCl_3$) δ 7.59 (dd, J=7.7, 1.6 Hz, 2H), 7.48-7.44 (m, 3H), 7.38 (tdd, J=7.0, 4.9, 1.9 Hz, 3H), 7.30 (dd, J=7.8, 1.7 Hz, 2H), 7.28-7.24 (m, 3H), 7.22 (dd, J=6.4, 3.3 Hz, 2H), 4.67 (s, 2H), 4.48 (s, 2H), 3.97 (q, J=7.1 Hz, 2H), 2.62 (s, 3H), 1.11 (t, J=7.1 Hz, 3H). $^{13}$C NMR (125 MHz, $CDCl_3$) δ 158.49, 148.33, 142.85, 136.22, 131.42, 129.58, 129.34, 129.22, 129.02, 128.75, 128.70, 128.22, 127.89, 127.50, 122.43, 60.68, 59.13, 55.62, 14.95, 13.89.)

Step 4: Synthesis of 1-benzyl-6-(methylthio)-3,5-diphenyl-3,5-dihydroimidazolo[4,5-c][1,2]thiazine-4 (1H)-one 2,2-dioxide

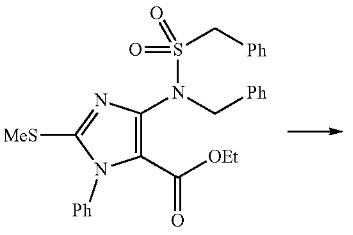

8-1

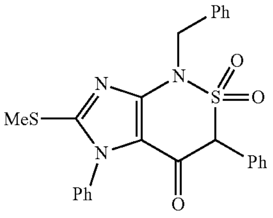

9-1

A solution obtained by dissolving a compound (175 mg, 0.336 mmol) represented by Chemical Formula 8-1 in DMF (3 mL) was cooled to 0° C., NaH (27 mg, 0.672 mmol) was added, and the mixture was stirred at room temperature for 1 hour. After the end of the reaction, the reaction mixture was concentrated, separated and purified by column chromatography on silica gel under a mixed solvent of hexane/ethyl acetate (1/2, v/v) to obtain white solid 1-benzyl-6-(methylthio)-3,5-diphenyl-3,5-dihydroimidazolo[4,5-c][1,2]thiazine-4(1H)-one 2,2-dioxide (152 mg, 95%) represented by Chemical Formula 9-1. ($^1$H NMR (500 MHz, $CDCl_3$) δ 7.48-7.43 (m, 5H), 7.37 (dd, J=8.5, 6.1 Hz, 1H), 7.34-7.28 (m, 7H), 7.25 (dd, J=6.1, 2.6 Hz, 2H), 5.12 (s, 2H), 4.97 (s, 1H), 2.68 (s, 3H). $^{13}$C NMR (125 MHz, $CDCl_3$) δ 171.33, 155.38, 152.81, 136.27, 134.76, 130.85, 129.81, 129.44, 129.01, 128.60, 128.24, 127.10, 126.92, 75.46, 47.27, 14.81)

Step 5: Synthesis of 1-benzyl-3,5-diphenyl-6-(propylthio)-3,5-dihydroimidazolo[4,5-c][1,2]thiazine-4 (1H)-one 2,2-dioxide

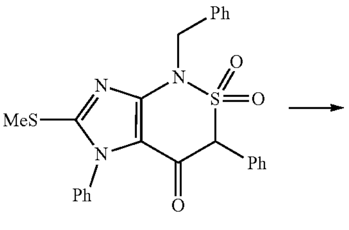

9-1

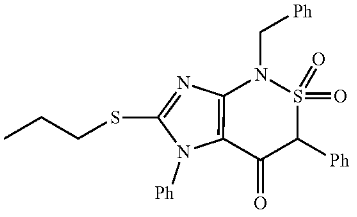

1-1

The compound (130 mg, 0.27 mmol) represented by Chemical Formula 9-1 was dissolved in a dichloromethane (5 mL) solution and stirred at room temperature for 10 minutes, meta-chlorobenzoic acid (m-CPBA; 182 mg, 0.81 mmol) was added at room temperature, and a reaction was followed while stirring at room temperature for 12 hours. After completion of a pseudoreaction using 10% sodium thiosulfonate solution, extraction was performed with water and ethyl acetate at room temperature, and the collected organic solution was dried and concentrated with anhydrous magnesium sulfate. The concentrated reaction mixture was dissolved in dichloromethane (3 mL) solution, propylthiol (0.87 mL, 0.95 mmol) and to triethylamine (1.35 mL, 0.95 mmol) were added at room temperature, and then a reaction was performed while stirring at room temperature for 2 hours. After the end of the reaction, the reaction mixture obtained by concentration was separated and purified by column chromatography on silica gel under a mixed solvent of hexane/ethyl acetate (1/3, v/v) to obtain yellow solid 1-benzyl-3,5-diphenyl-6-(propylthio)-3,5-dihydroimidazolo [4,5-c][1,2]thiazine-4(1H)-one 2,2-dioxide (Example 1-1; 150 mg, 94%) represented by Chemical Formula 1-1 ($^1$H NMR (500 MHz, $CDCl_3$) δ 7.45 (dd, J=4.3, 2.5 Hz, 5H), 7.42-7.35 (m, 2H), 7.31 (dt, J=4.6, 3.4 Hz, 7H), 7.27 (s, 1H), 5.11 (s, 2H), 4.98 (s, 1H), 3.22 (td, J=7.2, 3.8 Hz, 2H), 1.85-1.74 (m, 2H), 1.04 (t, J=7.4 Hz, 3H). $^{13}$C NMR (125 MHz, $CDCl_3$) δ 171.16, 152.82, 136.33, 130.90, 129.78, 129.38, 129.01, 128.57, 128.21, 127.12, 127.03, 75.48, 47.30, 34.45, 23.15, 13.48; LC-MS (ESI) m/z 505 ([M+1]$^+$)).

Example 2. Synthesis of Polysubstituted imidazolo[4,5-c][1,2]thiazine (Chemical Formulas 1-1 to 1-52)

In the compound represented by Chemical Formula 1, except that $R^1$, $R^2$, $R^3$, $R^4$, and $R^5$ were subjected to the experiment in the same manner as listed in Table 1 below, the same method as Example 1 above was performed to synthesize the polysubstituted imidazolo[4,5-c][1,2]thiazine derivative. In addition, the analysis results of synthesized polysubstituted imidazolo[4,5-c][1,2]thiazine derivative are shown in Table 1.

In addition, the degree of reaction progressed was determined by the TLC method in the middle of the preparation process for the polysubstituted imidazolo[4,5-c][1,2]thiazine derivative compound represented by Chemical Formula 1 according to the present disclosure, and the resulting compound represented by the Chemical Formula 1 was separated and purified, the structure was analyzed and identified by NMR or mass spectra, and the results are shown in Table 1.

TABLE 1

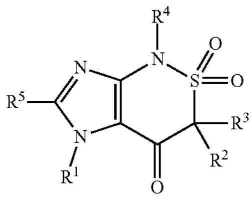

[Chemical Formula 1]

| Compound | $R^1$ | $R^2$ | $R^3$ | $R^4$ | $R^5$ | Analysis Data [$^1$H NMR (500 MHZ, $CDCl_3$) & LC/MS (ESI)] |
|---|---|---|---|---|---|---|
| 1-1 | Ph | Ph | H | Bn | n-PrS- | $^1$H NMR δ 7.45 (dd, J = 4.3, 2.5 Hz, 5H), 7.42-7.35 (m, 2H), 7.31 (dt, J = 4.6, 3.4 Hz, 7H), 7.27 (s, 1H), 5.11 (s, 2H), 4.98 (s, 1H), 3.22 (td, J = 7.2, 3.8 Hz, 2H), 1.85-1.74 (m, 2H), 1.04 (t, J = 7.4 Hz, 3H). $^{13}$C NMR (125 MHZ, $CDCl_3$) δ 171.16, 152.82, 136.33, 130.90, 129.78, 129.38, 129.01, 128.57, 128.21, 127.12, 127.03, 75.48, 47.30, 34.45, 23.15, 13.48.; LC-MS (ESI) m/z 505 ($[M + 1]^+$) |
| 1-2 | Ph | Ph | H | Bn | BnNH- | $^1$H NMR δ 7.45 (d, J = 7.8 Hz, 2H), 7.42 (dd, J = 5.8, 3.9 Hz, 3H), 7.35 (dd, J = 9.8, 7.7 Hz, 5H), 7.30 (d, J = 7.7 Hz, 3H), 7.28-7.27 (m, 3H), 5.08 (s, 2H), 4.95 (s, 1H), 4.88 (t, J = 5.8 Hz, 1H), 4.68-4.64 (m, 2H) LC-MS (ESI) m/z 535 ($[M + 1]^+$) |
| 1-3 | Ph | H | H | Bn | MeS- | $^1$H NMR δ 7.58-7.55 (m, 2H), 7.50-7.47 (m, 3H), 7.39-7.29 (m, 5H), 5.15 (s, 2H), 4.04 (s, 2H), 2.65 (s, 3H) LC-MS (ESI) m/z 400 ($[M + 1]^+$) |
| 1-4 | Ph | H | H | Bn | n-PrS- | $^1$H NMR δ 7.56 (d, J = 7.0 Hz, 2H), 7.50-7.45 (m, 3H), 7.39-7.28 (m, 5H), 5.13 (s, 2H), 4.05 (s, 2H), 3.24-3.14 (t, 2H), 1.75 (dd, J = 14.6, 7.3 Hz, 2H), 1.01 (t, J = 7.4 Hz, 3H) LC-MS (ESI) m/z 428 ($[M + 1]^+$) |
| 1-5 | Ph | Ph | H | Bn | n-BuNH- | $^1$H NMR δ 7.50-7.40 (m, 5H), 7.30 (ddd, J = 14.6, 8.4, 2.9 Hz, 10H), 5.07 (d, J = 2.4 Hz, 2H), 4.93 (s, 1H), 4.53 (t, J = 6.0 Hz, 1H), 3.47 (td, J = 7.2, 1.8 Hz, 2H), 1.59 (dt, J = 14.8, 7.2 Hz, 2H), 1.37 (dt, J = 14.9, 7.4 Hz, 2H),0.96 (t, J = 7.4 Hz, 3H) LC-MS (ESI) m/z 501 ($[M + 1]^+$) |
| 1-6 | Ph | H | H | Bn | n-BuNH- | $^1$H NMR δ 7.58 (d, J = 7.0 Hz, 2H), 7.50 (t, J = 7.4 Hz, 2H), 7.45 (dd, J = 8.8, 5.9 Hz, 1H), 7.36 (t, J = 7.2 Hz, 2H), 7.33-7.29 (m, 3H), 5.11 (s, 2H), 4.50 (t, J = 5.8 Hz, 1H), 4.00 (s, 2H), 3.43 (dd, J = 13.4, 6.9 Hz, 2H), 1.55 (dt, J = 14.8, 7.4 Hz, 2H), 1.33 (dq, J = 14.7, 7.4, Hz, 2H), 0.94 (t, J = 7.4 Hz, 3H) LC-MS (ESI) m/z 505 ($[M + 1]^+$) |
| 1-7 | Ph | Ph | H | Et | $MeSO_2$- | $^1$H NMR δ 7.56-7.44 (m, 5H), 7.44-7.38 (m, 3H), 7.32-7.28 (m, 2H), 5.08 (s, 1H), 4.11 (dt, J = 14.1, 5.9 Hz, 2H), 3.39 (s, 3H), 1.43 (t, J = 7.1 Hz, 3H) LC-MS (ESI) m/z 446 ($[M + 1]^+$) |
| 1-8 | Ph | Et | H | Bn | MeS- | $^1$H NMR δ 7.59 (d, J = 7.0 Hz, 2H), 7.50-7.46 (m, 3H), 7.36 (d, J = 7.7 Hz, 2H), 7.34-7.28 (m, 3H), 5.13 (s, 2H), 3.65 (dd, J = 7.4, 5.9 Hz, 1H), 2.64 (s, 3H), 2.16-2.07 (m, 1H), 1.96 (dt, J = 22.2, 7.5 Hz, 1H), 1.11 (t, J = 7.5, 3H) LC-MS (ESI) m/z 428 ($[M + 1]^+$) |

TABLE 1-continued

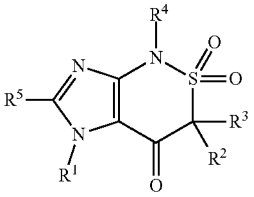

[Chemical Formula 1]

| Compound | $R^1$ | $R^2$ | $R^3$ | $R^4$ | $R^5$ | Analysis Data [$^1$H NMR (500 MHZ, $CDCl_3$) & LC/MS (ESI)] |
|---|---|---|---|---|---|---|
| 1-9 | Ph | Ph | H | Bn | MeS- | $^1$H NMR δ 7.48-7.43 (m, 5H), 7.37 (dd, J = 8.5, 6.1 Hz, 1H), 7.34-7.28 (m, 7H), 7.25 (dd, J = 6.1, 2.6 Hz, 2H), 5.12 (s, 2H), 4.97 (s, 1H), 2.68 (s, 3H) LC-MS (ESI) m/z 476 ([M + 1]$^+$) |
| 1-10 | Ph | Ph | H | Bn | $MeSO_2$- | $^1$H NMR δ 7.54-7.40 (m, 8H), 7.35 (dt, J = 6.3, 4.2 Hz, 5H), 7.25-7.21 (m, 2H), 5.14 (d, J = 1.9 Hz, 2H), 5.03 (s, 1H), 3.38 (s, 3H) LC-MS (ESI) m/z 508 ([M + 1]$^+$) |
| 1-11 | Ph | Ph | H | Et | PhS- | $^1$H NMR δ 7.52-7.44 (m, 5H), 7.42-7.29 (m, 10H), 5.00 (s, 1H), 3.94 (q, J = 7.1 Hz, 2H), 1.29 (t, J = 7.1 Hz, 3H) LC-MS (ESI) m/z 476 ([M + 1]$^+$) |
| 1-12 | Ph | Ph | H | Et | n-PrS- | $^1$H NMR δ 7.47 (dd, J = 5.2, 1.8 Hz, 3H), 7.42-7.30 (m, 7H), 4.99 (s, 1H), 4.06 (q, J = 7.1 Hz, 2H), 3.24 (td, J = 7.1, 3.5 Hz, 2H), 1.80 (dd, J = 14.6, 7.3 Hz, 2H), 1.41 (t, J = 7.1 Hz, 3H), 1.04 (t, J = 7.4 Hz, 3H) LC-MS (ESI) m/z 442 ([M + 1]$^+$) |
| 1-13 | Ph | Ph | H | Et | n-BuNH- | $^1$H NMR δ 7.51-7.46 (m, 2H), 7.44 (dt, J = 9.6, 4.3 Hz, 1H), 7.40-7.29 (m, 7H), 4.94 (s, 1H), 4.51 (t, J = 5.8 Hz, 1H), 4.02 (q, J = 7.1 Hz, 2H), 3.47 (ddd, J = 13.0, 7.0, 3.0 Hz, 2H), 1.57 (dd, J = 15.0, 7.4 Hz, 2H), 1.43-1.29 (m, 5H), 0.95 (t, J = 7.4 Hz, 3H) LC-MS (ESI) m/z 439 ([M + 1]$^+$) |
| 1-14 | Ph | Ph | H | Et | BnNH- | $^1$H NMR δ 7.47 (dd, J = 8.2, 6.7 Hz, 2H), 7.42 (d, J = 7.4 Hz, 1H), 7.39-7.34 (m, 8H), 7.33 (t, J = 5.3 Hz, 4H), 4.96 (s, 1H), 4.84 (d, J = 5.9 Hz, 1H), 4.67 (t, J = 5.8 Hz, 2H), 4.03 (q, J = 7.1 Hz, 2H), 1.39 (t, J = 7.1 Hz, 3H) LC-MS (ESI) m/z 473 ([M + 1]$^+$) |
| 1-15 | Ph | Ph | H | Bn | PhS- | $^1$H NMR δ 7.60-7.55 (m, 2H), 7.48 (ddd, J = 7.3, 5.5, 3.7 Hz, 6H), 7.34 (ddd, J = 16.7, 10.9, 4.4 Hz, 7H), 7.22 (dd, J = 15.1, 8.7 Hz, 5H), 4.97 (s, 1H), 4.90 (s, 2H) LC-MS (ESI) m/z 538 ([M + 1]$^+$) |
| 1-16 | Ph | 4-Cl-Ph | H | Bn | n-PrS- | $^1$H NMR δ 7.53-7.41 (m, 5H), 7.38-7.30 (m, 5H), 7.30-7.27 (m, 2H), 7.22-7.14 (m, 2H), 5.11 (d, J = 5.5 Hz, 2H), 4.95 (s, 1H), 3.23 (td, J = 7.1, 1.4 Hz, 2H), 1.80 (dd, J = 14.6, 7.3 Hz, 2H), 1.05 (t, J = 7.4 Hz, 3H) LC-MS (ESI) m/z 539 ([M + 1]$^+$) |
| 1-17 | Ph | 4-Cl-Ph | H | Bn | PhS- | $^1$H NMR δ 7.58 (dd, J = 8.2, 1.4 Hz, 2H), 7.49 (ddd, J = 7.3, 6.9, 3.7 Hz, 6H), 7.35 (dd, J = 6.3, 2.6 Hz, 2H), 7.31-7.26 (m, 3H), 7.20 (ddd, J = 10.8, 8.1, 4.4 Hz, 6H), 4.94 (s, 1H), 4.90 (d, J = 4.8 Hz, 2H) LC-MS (ESI) m/z 573 ([M + 1]$^+$) |
| 1-18 | Ph | 4-Cl-Ph | H | Bn | n-BuNH- | $^1$H NMR δ 7.50-7.41 (m, 5H), 7.33-7.28 (m, 5H), 7.24 (dt, J = 9.1, 2.2 Hz, 2H), 7.19-7.15 (m, 2H), 5.07 (d, J = 2.6 Hz, 2H), 4.90 (s, 1H), 4.59 (t, J = 5.9 Hz, 1H), 3.47 (dd, J = 13.3, 7.0 Hz, 2H), 1.62-1.54 (m, 2H), 1.36 (dd, J = 15.0, 7.4 Hz, 2H), 0.96 (t, J = 7.4 Hz, 3H) LC-MS (ESI) m/z 536 ([M + 1]$^+$) |

TABLE 1-continued

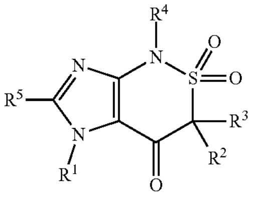

[Chemical Formula 1]

| Compound | $R^1$ | $R^2$ | $R^3$ | $R^4$ | $R^5$ | Analysis Data [$^1H$ NMR (500 MHZ, $CDCl_3$) & LC/MS (ESI)] |
|---|---|---|---|---|---|---|
| 1-19 | Ph | 4-Cl-Ph | H | Bn | BnNH- | $^1H$ NMR δ 7.48-7.43 (m, 2H), 7.43-7.39 (m, 3H), 7.37-7.33 (m, 4H), 7.32-7.26 (m, 7H), 7.24-7.22 (m, 1H), 7.19-7.15 (m, 2H), 5.07 (d, J = 5.3 Hz, 2H), 4.93 (t, J = 6.0 Hz, 1H), 4.91 (s, 1H), 4.66 (dd, J = 5.9, 4.3 Hz, 2H) LC-MS (ESI) m/z 570 ([M + 1]$^+$) |
| 1-20 | Ph | 4-Cl-Ph | H | Et | n-PrS- | $^1H$ NMR δ 7.48 (dd, J = 5.0, 1.8 Hz, 3H), 7.40-7.31 (m, 4H), 7.29-7.26 (m, 2H), 4.99 (s, 1H), 4.08 (d, J = 7.1 Hz, 2H), 3.24 (dd, J = 10.8, 3.7 Hz, 2H), 1.80 (dd, J = 14.5, 7.3 Hz, 2H), 1.44 (t, J = 7.1 Hz, 3H), 1.03 (t, J = 7.4 H, 3H) LC-MS (ESI) m/z 477 ([M + 1]$^+$) |
| 1-21 | Ph | 4-Cl-Ph | H | Et | PhS- | $^1H$ NMR δ 7.48 (dt, J = 8.6, 2.1 Hz, 2H), 7.46-7.41 (m, 1H), 7.34 (ddd, J = 7.0, 4.5, 1.8 Hz, 4H), 7.28 (dd, J = 8.6, 2.1 Hz, 2H), 4.93 (s, 1H), 4.56 (s, 1H), 4.03 (q, J = 7.1 Hz, 2H), 3.46 (td, J = 7.0, 1.0 Hz, 2H), 1.61-1.52 (m, 2H), 1.39 (dd, J = 9.2, 4.9 Hz, 3H), 1.37-1.32 (m, 2H), 0.97-0.93 (m, 3H) LC-MS (ESI) m/z 511 ([M + 1]$^+$) |
| 1-22 | Ph | 4-Cl-Ph | H | Et | n-BuNH- | $^1H$ NMR δ 7.48 (dt, J = 8.6, 2.1 Hz, 2H), 7.46-7.41 (m, 1H), 7.34 (ddd, J = 7.0, 4.5, 1.8 Hz, 4H), 7.28 (dd, J = 8.6, 2.1 Hz, 2H), 4.93 (s, 1H), 4.56 (s, 1H), 4.03 (q, J = 7.1 Hz, 2H), 3.46 (td, J = 7.0, 1.0 Hz, 2H), 1.61-1.52 (m, 2H), 1.39 (dd, J = 9.2, 4.9 Hz, 3H), 1.37-1.32 (m, 2H), 0.97-0.93 (m, 3H) LC-MS (ESI) m/z 473 ([M + 1]$^+$) |
| 1-23 | Ph | 4-Cl-Ph | H | Et | BnNH- | $^1H$ NMR δ 7.49-7.45 (m, 2H), 7.44-7.39 (m, 1H), 7.36-7.31 (m, 8H), 7.30-7.27 (m, 3H), 4.94 (s, 1H), 4.88 (d, J = 5.9 Hz, 1H), 4.65 (dd, J = 5.9, 3.2 Hz, 2H), 4.04 (q, J = 7.0 Hz, 2H), 1.40 (t, J = 7.1 Hz, 3H) LC-MS (ESI) m/z 508 ([M + 1]$^+$) |
| 1-24 | Ph | 4-Cl-Ph | Me | Bn | n-PrS- | $^1H$ NMR δ 7.53 (dd, J = 5.2, 1.9 Hz, 3H), 7.41-7.36 (m, 2H), 7.34-7.31 (m, 2H), 7.30-7.28 (m, 2H), 7.27-7.24 (m, 5H), 5.05 (s, 2H), 3.23 (td, J = 7.1, 2.5 Hz, 2H), 1.97 (s, 3H), 1.81 (dd, J = 14.6, 7.3 Hz, 2H), 1.06 (t, J = 7.4 Hz, 3H) LC-MS (ESI) m/z 553 ([M + 1]$^+$) |
| 1-25 | Me | Ph | H | Bn | n-PrS- | $^1H$ NMR δ 7.37 (dddd, J = 21.9, 15.1, 6.3, 1.5 Hz, 5H), 7.26 (d, J = 1.3 Hz, 2H), 7.24 (dd, J = 6.8, 1.5 Hz, 3H), 5.02 (s, 2H), 4.96 (s, 1H), 3.78 (s, 3H), 3.27 (td, J = 7.2, 3.9 Hz, 2H), 1.82 (dd, J = 14.6, 7.3 Hz, 2H), 1.08 (t, J = 7.4 Hz, 3H) LC-MS (ESI) m/z 442 ([M + 1]$^+$) |
| 1-26 | Me | Ph | H | Bn | PhS- | $^1H$ NMR δ 7.59-7.54 (m, 2H), 7.48-7.38 (m, 4H), 7.33 (dd, J = 10.4, 4.8 Hz, 2H), 7.24 (dd, J = 10.3, 3.8 Hz, 3H), 7.21-7.16 (m, 4H), 4.95 (s, 1H), 4.90 (s, 2H), 3.89 (s, 3H) LC-MS (ESI) m/z 476 ([M + 1]$^+$) |

TABLE 1-continued

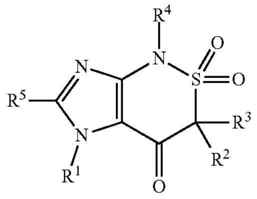

[Chemical Formula 1]

| Compound | $R^1$ | $R^2$ | $R^3$ | $R^4$ | $R^5$ | Analysis Data [$^1$H NMR (500 MHZ, $CDCl_3$) & LC/MS (ESI)] |
|---|---|---|---|---|---|---|
| 1-27 | Me | Ph | H | Bn | n-BuNH- | $^1$H NMR δ 7.36 (ddd, J = 6.2, 3.9, 1.6 Hz, 3H), 7.29 (t, J = 7.6 Hz, 2H), 7.26-7.21 (m, 5H), 4.98 (d, J = 3.6 Hz, 2H), 4.91 (s, 2H), 4.42 (s, 1H), 3.59 (s, 3H), 3.50 (dd, J = 5.7, 1.6 Hz, 2H), 1.67-1.59 (m, 2H), 1.43 (dd, J = 15.0, 7.5 Hz, 2H), 0.99 (t, J = 7.4 Hz, 3H) LC-MS (ESI) m/z 439 ([M + 1]$^+$) |
| 1-28 | Me | Ph | H | Bn | BnNH- | $^1$H NMR δ 7.37-7.27 (m, 9H), 7.25-7.21 (m, 2H), 7.19 (t, J = 7.7 Hz, 4H), 5.15 (d, J = 5.9 Hz, 1H), 4.96 (d, J = 1.7 Hz, 2H), 4.84 (s, 1H), 4.61 (t, J = 5.7 Hz, 2H), 3.48 (s, 3H) LC-MS (ESI) m/z 473 ([M + 1]$^+$) |
| 1-29 | Me | Ph | H | Et | n-PrS- | $^1$H NMR δ 7.44-7.37 (m, 3H), 7.35-7.31 (m, 2H), 4.98 (s, 1H), 4.04-3.92 (m, 2H), 3.81 (s, 3H), 3.37-3.18 (m, 2H), 1.83 (dd, J = 14.6, 7.3 Hz, 2H), 1.32 (t, J = 7.1 Hz, 3H), 1.07 (t, J = 7.4 Hz, 3H) LC-MS (ESI) m/z 380 ([M + 1]$^+$) |
| 1-30 | Me | Ph | H | Et | PhS- | $^1$H NMR δ 7.53-7.48 (m, 2H), 7.45-7.37 (m, 6H), 7.35-7.30 (m, 2H), 5.01 (s, 1H), 3.96-3.92 (m, 2H), 3.91 (s, 3H), 1.26 (td, J = 7.1, 2.4 Hz, 3H) LC-MS (ESI) m/z 414 ([M + 1]$^+$) |
| 1-31 | Me | Ph | H | Et | n-BuNH- | $^1$H NMR δ 7.40-7.34 (m, 3H), 7.34-7.30 (m, 2H), 4.90 (s, 1H), 4.68 (t, J = 5.7 Hz, 1H), 3.92 (qd, J = 7.1, 1.4 Hz, 2H), 3.58 (s, 3H), 3.50-3.40 (m, 2H), 1.67-1.54 (m, 2H), 1.43-1.37 (m, 2H), 1.28 (t, J = 7.1 Hz, 3H), 0.97 (t, J = 3H) LC-MS (ESI) m/z 377 ([M + 1]$^+$) |
| 1-32 | Me | Ph | H | Et | BnNH- | $^1$H NMR δ 7.42-7.34 (m, 7H), 7.34-7.28 (m, 3H), 5.04 (d, J = 5.8 Hz, 1H), 4.87 (s, 1H), 4.65 (t, J = 6.2 Hz, 2H), 4.00-3.85 (m, 2H), 3.56 (s, 3H), 1.29 (t, J = 7.1 Hz, 3H) LC-MS (ESI) m/z 411 ([M + 1]$^+$) |
| 1-33 | Me | 4-Cl-Ph | H | Bn | n-PrS- | $^1$H NMR δ 7.37-7.33 (m, 2H), 7.29-7.25 (m, 5H), 7.18-7.13 (m, 2H), 5.02 (d, J = 5.5 Hz, 2H), 4.92 (s, 1H), 3.77 (s, 3H), 3.28 (td, J = 7.1, 1.8 Hz, 2H), 1.82 (dd, J = 14.6, 7.3 Hz, 2H), 1.08 (t, J = 7.4 Hz, 3H) LC-MS (ESI) m/z 477 ([M + 1]$^+$) |
| 1-34 | Me | 4-Cl-Ph | H | Bn | PhS- | $^1$H NMR δ 7.57 (dd, J = 7.5, 2.1 Hz, 2H), 7.49-7.43 (m, 3H), 7.31-7.27 (m, 2H), 7.26 (s, 1H), 7.21-7.12 (m, 6H), 4.95-4.84 (m, 3H), 3.88 (s, 3H) LC-MS (ESI) m/z 511 ([M + 1]$^+$) |
| 1-35 | Me | 4-Cl-Ph | H | Bn | n-BuNH- | $^1$H NMR δ 7.35 (dd, J = 7.8, 1.6 Hz, 2H), 7.27 (s, 1H), 7.26-7.21 (m, 4H), 7.17-7.12 (m, 2H), 4.99 (d, J = 3.7 Hz, 2H), 4.87 (s, 1H), 4.31 (t, J = 5.8 Hz, 1H), 3.62 (s, 3H), 3.53 (dd, J = 5.8, 1.4 Hz, 2H), 1.71-1.60 (m, 2H), 1.44 (dd, J = 15.0, 7.5 Hz, 2H), 1.00 (t, J = 7.4 Hz, 3H) LC-MS (ESI) m/z 473 ([M + 1]$^+$) |
| 1-36 | Me | 4-Cl-Ph | H | Bn | BnNH- | $^1$H NMR δ 7.41-7.34 (m, 5H), 7.33-7.28 (m, 3H), 7.26-7.19 (m, 4H), 7.15 (d, J = 8.5 Hz, 2H), 5.00 (d, J = 6.0 Hz, 2H), 4.88 (s, 1H), 4.70 (t, J = 5.7 Hz, 2H), 4.67-4.63 (m, 1H), 3.64 (s, 3H) LC-MS (ESI) m/z 508 ([M + 1]$^+$) |

TABLE 1-continued

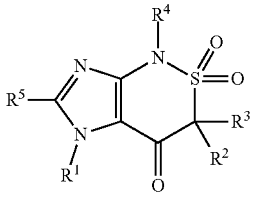

[Chemical Formula 1]

| Compound | $R^1$ | $R^2$ | $R^3$ | $R^4$ | $R^5$ | Analysis Data [$^1$H NMR (500 MHZ, $CDCl_3$) & LC/MS (ESI)] |
|---|---|---|---|---|---|---|
| 1-37 | Me | 4-Cl-Ph | H | Et | n-PrS- | $^1$H NMR δ 7.42-7.34 (m, 2H), 7.31-7.27 (m, 2H), 4.96 (s, 1H), 3.99 (q, J = 7.1 Hz, 2H), 3.81 (s, 3H), 3.28 (td, J = 7.1, 3.1 Hz, 2H), 1.83 (dd, J = 14.6, 7.3 Hz, 2H), 1.35 (t, J = 7.1 Hz, 3H), 1.07 (t, J = 7.4 Hz, 3H)<br>LC-MS (ESI) m/z 414 ([M + 1]$^+$) |
| 1-38 | Me | 4-Cl-Ph | H | Et | PhS- | $^1$H NMR δ 7.54-7.48 (m, 2H), 7.42-7.36 (m, 5H), 7.29-7.26 (m, 2H), 4.98 (s, 1H), 3.93 (q, J = 7.1 Hz, 2H), 3.90 (s, 3H), 1.28 (t, J = 7.1 Hz, 3H)<br>LC-MS (ESI) m/z 448 ([M + 1]$^+$) |
| 1-39 | Me | 4-Cl-Ph | H | Et | n-BuNH- | $^1$H NMR δ 7.38-7.34 (m, 2H), 7.30-7.26 (m, 2H), 4.90 (s, 1H), 4.32 (s, 1H), 3.94 (q, J = 7.1 Hz, 2H), 3.65 (s, 3H), 3.58-3.45 (m, 2H), 1.69-1.60 (m, 2H), 1.46-1.39 (m, 2H), 1.31 (t, J = 7.1 Hz, 3H), 0.99 (t, J = 7.4 Hz, 3H)<br>LC-MS (ESI) m/z 411 ([M + 1]$^+$) |
| 1-40 | Me | 4-Cl-Ph | H | Et | BnNH- | $^1$H NMR δ 7.41-7.34 (m, 6H), 7.29 (d, J = 8.4 Hz, 3H), 4.91 (s, 1H), 4.68 (d, J = 5.8 Hz, 2H), 4.60 (t, J = 5.6 Hz, 1H), 3.96 (d, J = 7.1 Hz, 2H), 3.66 (s, 3H), 1.32 (t, J = 7.1 Hz, 3H)<br>LC-MS (ESI) m/z 445 ([M + 1]$^+$) |
| 1-41 | Me | 4-Cl-Ph | H | Bn | 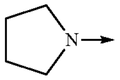 | $^1$H NMR δ 7.34 (dd, J = 7.6, 1.8 Hz, 2H), 7.27 (d, J = 0.9 Hz, 1H), 7.24 (ddd, J = 5.9, 4.6, 2.5 Hz, 4H), 7.18-7.14 (m, 2H), 4.96 (s, 2H), 4.88 (s, 1H), 3.83 (s, 3H), 3.68 (t, J = 6.7 Hz, 4H), 2.04-1.98 (m, 4H)<br>LC-MS (ESI) m/z 471 ([M + 1]$^+$) |
| 1-42 | Me | 4-Cl-Ph | H | Et | 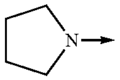 | $^1$H NMR δ 7.38-7.34 (m, 2H), 7.30-7.27 (m, 2H), 4.89 (s, 1H), 3.91 (d, J = 7.1 Hz, 2H), 3.85 (s, 3H), 3.67 (dd, J = 7.9, 6.5 Hz, 4H), 2.04-1.96 (m, 4H), 1.29 (dd, J = 12.8, 5.7 Hz, 3H)<br>LC-MS (ESI) m/z 409 ([M + 1]$^+$) |
| 1-43 | Ph | Ph | H | Bn | 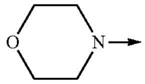 | $^1$H NMR δ 7.47-7.33 (m, 9H), 7.32-7.27 (m, 5H), 7.25 (s, 1H), 5.06 (d, J = 2.6 Hz, 2H), 4.93 (s, 1H), 3.65-3.53 (m, 4H), 3.23 (dd, J = 7.2, 4.1 Hz, 4H)<br>LC-MS (ESI) m/z 515 ([M + 1]$^+$) |
| 1-44 | Ph | Me | Me | Et | MeS- | $^1$H NMR δ 7.49 (dd, J = 4.9, 1.7 Hz, 3H), 7.33 (dd, J = 6.7, 2.9 Hz, 2H), 4.10 (q, J = 7.1 Hz, 2H), 2.64 (s, 3H), 1.57 (s, 6H), 1.48 (t, J = 7.1 Hz, 3H)<br>LC-MS (ESI) m/z 366 ([M + 1]$^+$) |
| 1-45 | Ph | Me | H | Et | MeS- | $^1$H NMR δ 7.53-7.45 (m, 3H), 7.36-7.30 (m, 2H), 4.11 (q, J = 7.1 Hz, 2H), 3.87 (d, J = 7.2 Hz, 1H), 2.65 (s, 3H), 1.62 (d, J = 7.2 Hz, 3H), 1.48 (t, J = 7.1 Hz, 3H)<br>LC-MS (ESI) m/z 352 ([M + 1]$^+$) |
| 1-46 | Ph | Bn | H | Bn | MeS- | $^1$H NMR δ 7.60-7.54 (m, 2H), 7.50-7.45 (m, 3H), 7.34 (ddd, J = 14.4, 7.7, 2.0 Hz, 3H), 7.30-7.27 (m, 2H), 7.22 (ddd, J = 12.2, 7.7, 5.9 Hz, 5H), 5.26-4.94 (m, 3H), 3.35 (dd, J = 12.8, 6.0 Hz, 2H), 2.63 (s, 3H)<br>LC-MS (ESI) m/z 490 ([M + 1]$^+$) |

TABLE 1-continued

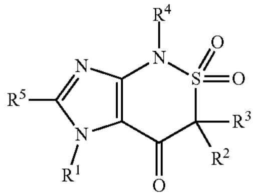

[Chemical Formula 1]

| Compound | $R^1$ | $R^2$ | $R^3$ | $R^4$ | $R^5$ | Analysis Data [$^1$H NMR (500 MHZ, $CDCl_3$) & LC/MS (ESI)] |
|---|---|---|---|---|---|---|
| 1-47 | Ph | Ph | 4-MeO-Bn | Bn | MeS- | $^1$H NMR δ 7.52-7.40 (m, 7H), 7.34-7.30 (m,12H), 7.30-7.24 (m, 7H), 6.89-6.79 (m, 2H), 6.68-6.56 (m, 2H), 4.99 (dd, J = 51.2, 15.1 Hz, 2H), 3.77-3.67 (m, 5H), 2.57 (s, 3H) LC-MS (ESI) m/z 596 ([M + 1]$^+$) |
| 1-48 | Me | Ph | H | Me | n-PrS- | $^1$H NMR δ 7.41 (dd, J = 7.0, 5.5 Hz, 3H), 7.35 (dd, J = 7.8, 1.7 Hz, 2H), 5.03 (s, 1H), 3.81 (s, 3H), 3.40 (s, 3H), 3.29 (td, J = 7.1, 4.3 Hz, 2H), 1.83 (dd, J = 14.6, 7.3 Hz, 2H), 1.26 (dd, J = 8.3, 5.9 Hz, 2H), 1.07 (t, J = 7.4 Hz, 3H) LC-MS (ESI) m/z 366 ([M + 1]$^+$) |
| 1-49 | Me | Ph | H | Me | PhS- | $^1$H NMR δ 7.52-7.49 (m, 2H), 7.44-7.39 (m, 6H), 7.35 (dd, J = 7.9, 1.6 Hz, 2H), 5.06 (s, 1H), 3.91 (s, 3H), 3.35 (s, 3H) LC-MS (ESI) m/z 400 ([M + 1]$^+$) |
| 1-50 | Me | Ph | H | Me | BnNH- | $^1$H NMR δ 7.40 (td, J = 5.4, 2.6 Hz, 7H), 7.38-7.35 (m, 3H), 4.99 (s, 1H), 4.70 (d, J = 5.9 Hz, 2H), 4.53-4.50 (m, 1H), 3.68 (s, 3H), 3.37 (s, 3H) LC-MS (ESI) m/z 397 ([M + 1]$^+$) |
| 1-51 | Me | Ph | H | Bn | MeS- | $^1$H NMR δ 7.62-6.91 (m, 12H), 5.04 (s, 2H), 4.95 (s, 1H), 3.78 (s, 3H), 2.74 (s, 3H), 1.55 (s, 2H) LC-MS (ESI) m/z 414 ([M + 1]$^+$) |
| 1-52 | Me | Ph | H | Me | $MeSO_2$- | $^1$H NMR δ 7.54-7.41 (m, 3H), 7.34 (dd, J = 8.0, 1.4 Hz, 2H), 5.13 (s, 1H), 4.28 (s, 3H), 3.46 (s, 3H), 3.43 (s, 3H) LC-MS (ESI) m/z 370 ([M + 1]$^+$) |

Example 3. Identification of Increased Survival Rate in Cecal Ligation and Puncture (CLP)-Induced Sepsis Mouse Models The anti-inflammatory efficacy of the prepared compound was tested by the survival rate of peritonitis-induced sepsis mouse model. CLP-induced sepsis mouse models were prepared by in vivo methods to verify anti-inflammatory activity, and the preparation method is a widely used experimental method [Wang H, Nat. Med., 2004, 10, 1216-1221]. Forty 6-week-old ICR male mice were divided into 10 mice in each group and the survival rate was observed.

First, the male mice were given respiratory anesthesia using isoflurane, an incision of about 2 cm was made in the middle of the abdomen to take out the appendix adjacent to the intestine, a 5.0. mm portion from the tip of the appendix was ligated with a 3.0-silk suture and pierced once with a 22-gauge needle, and then the incision was closed again with a 4.0-silk suture. Sham mice were sutured without tying or piercing the appendix after incision, and the compound prepared 12 hours and 50 hours after surgery was administered intravenously into mouse tail. The survival rate of mice was observed every 6 hours after surgery, and the results are shown in FIG. 1.

As shown in FIG. 1, 1-42 compounds showed that the survival rate of the CLP-induced sepsis mouse model was increased by 60% compared to a group of which only CLP was performed, while the other compounds also showed the survival rate of about 40%. This was comparable to the improvement effect of survival rate in the sepsis mouse models of FDA-approved activated protein A. Through the above experimental results, the anti-inflammatory effect of the polysubstituted imidazolo[4,5-c][1,2]thiazine derivative on vascular inflammatory diseases was identified.

PREPARATION EXAMPLE

Preparation Example 1. Preparation of Tablets (Pressing Method)

As an active ingredient, 5.0 mg of the compound represented by Chemical Formula 1 of the present disclosure was sieved, and then 14.1 mg of lactose, 0.8 mg of crospovidone USNF, and 0.1 mg of magnesium stearate were mixed and pressed into tablets.

Preparation Example 2. Preparation of Tablets (Wet Assembly)

As an active ingredient, 5.0 mg of the compound represented by Chemical Formula 1 of the present disclosure was sieved and mixed with 16.0 mg of lactose and 4.0 mg of starch. 0.3 mg of polysorbate 80 was dissolved in pure water, and then an appropriate amount of the solution was added for microparticulation. After drying, the microparticles were sieved and mixed with 2.7 mg of colloidal silicon dioxide and 2.0 mg of magnesium stearate. The microparticles were pressed to be prepared into tablets.

Preparation Example 3. Preparation of Powder and Capsules

As an active ingredient, 5.0 mg of the compound represented by Chemical Formula 1 of the present disclosure was sieved and mixed with 14.8 mg of lactose, 10.0 mg of polyvinyl pyrrolidone, and 0.2 mg of magnesium stearate. The mixture was filled in No. 5 hard gelatin capsules using a suitable device.

Preparation Example 4. Preparation of Injection

As an active ingredient, 100 mg of the compound represented by Chemical Formula 1 of the present disclosure was included, and moreover, an injection was prepared by including 180 mg of mannitol, 26 mg of $Na_2HPO_4*12H_2O$ and 2,974 mg of distilled water.

The foregoing description of the present disclosure is for illustrative purposes only, and a person skilled in the art to which the present disclosure pertains will be able to understand that it is easily transformable into other specific forms without changing the technical idea or essential features of the present disclosure. Therefore, the example embodiments described above should be understood as exemplary and not limited in all respects.

The invention claimed is:

1. A polysubstituted imidazolo[4,5-c][1,2]thiazine derivative represented by the following Chemical Formula 1 and a pharmaceutically acceptable salt thereof, or a stereoisomer thereof,

[Chemical Formula 1]

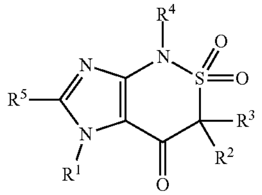

wherein:

$R^1$ is hydrogen, a linear, branched, or cyclic $C_3$~$C_{10}$ alkyl group; a phenyl group or $R^6$-substituted phenyl group; a benzyl group or $R^5$-substituted benzyl group; or a $R^5$-substituted or unsubstituted aromatic group, wherein the aromatic group represents a furanyl group, a thiophenyl group, a pyridinyl group, a pyridazinyl group, a naphthyl group, a quinolinyl group, or an isoquinolinyl group; and the $R^6$ is a 1 to 3 substituents selected from the group consisting of a hydrogen atom; a halogen atom; a hydroxy group; a cyano group; a nitro group; an amino group or amino group in which 1 to 2 linear, branched, or cyclic $C_3$~$C_{10}$ alkyl groups are substituted; a linear, branched, or cyclic $C_3$~$C_{10}$ alkyl group; a $C_1$~$C_{10}$ alkoxy group; a $C_1$~$C_{10}$ haloalkoxy group; a $C_1$~$C_{10}$ haloalkyl group; and an alkoxy group comprising a substituted or unsubstituted aromatic ring, $R^2$ and $R^3$ are independently substituted hydrogen, a linear, branched, or cyclic $C_3$-~$C_{10}$ alkyl group, a cyclic $C_3$~$C_{10}$ alkyl group comprising a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, $R^4$ is hydrogen, a linear, branched, or cyclic $C_3$~$C_6$ alkyl group, a cyclic $C_3$~$C_6$ alkyl group comprising a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, and $R^5$ represents one or more linear, branched, or cyclic $C_3$~$C_{10}$ alkyl groups, $C_3$~$C_{10}$ aryl groups, $C_3$~$C_{10}$ heteroaryl groups or substituted heteroaryl groups, amino groups substituted with $C_3$~$C_{10}$ aryl alkyl groups or $C_3$~$C_{10}$ heteroaryl alkyl groups, thio groups or phenyl groups substituted with $C_3$~$C_{10}$ aryl alkyl groups or $C_3$~$C_{10}$ heteroaryl alkyl groups, substituted phenyl groups, benzyl groups, substituted benzyl groups, linear, branched, or cyclic $C_3$~$C_{10}$ alkyl groups, or amines with piperazine

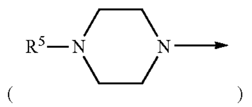

substituted with phenyl, heteroarylamide groups, wherein, in the $R^1$, $R^2$, $R^3$, and $R^4$, the substituted phenyl group, the substituted benzyl group, or the substituted $C_3$~$C_{10}$ heteroaryl group represents 1 to 4 substitutions of any one substituent selected from the group consisting of halogen atoms, nitro groups, $C_1$~$C_{10}$ alkyl groups, $C_1$~$C_{10}$ alkoxy groups, $C_1$~$C_{10}$ haloalkyl groups, and $C_1$~$C_{10}$ haloalkoxy groups.

2. The polysubstituted imidazolo[4,5-c][1,2]thiazine derivative and the pharmaceutically acceptable salt thereof, or the stereoisomer thereof of claim 1, wherein, in the Chemical Formula 1, $R^1$ is hydrogen, a linear, branched, or cyclic $C_3$~$C_7$ alkyl group; a phenyl group or $R^6$-substituted phenyl group; a benzyl group or $R^6$-substituted benzyl group; or a $R^5$-substituted or unsubstituted aromatic group, wherein the aromatic group represents a furanyl group, a thiophenyl group, a pyridinyl group, a pyridazinyl group, a naphthyl group, a quinolinyl group, or an isoquinolinyl group; and the $R^6$ is a 1 to 3 substituents selected from the group consisting of a hydrogen atom; a halogen atom; a hydroxy group; a cyano group; a nitro group; an amino group or amino group in which 1 to 2 linear, branched, or cyclic $C_3$~$C_5$ alkyl groups are substituted; a linear, branched, or cyclic $C_3$~$C_5$ alkyl group; a $C_1$~$C_5$ alkoxy group; a $C_1$~$C_5$ haloalkoxy group; a $C_1$~$C_5$ haloalkyl group; and an alkoxy group comprising a substituted or unsubstituted aromatic ring, $R^2$ and $R^3$ are independently substituted hydrogen, a linear, branched, or cyclic $C_3$~$C_7$ alkyl group, a cyclic $C_3$~$C_7$ alkyl group comprising a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, $R^4$ is hydrogen, a linear, branched, or cyclic $C_3$~$C_4$ alkyl group, a cyclic $C_3$~$C_4$ alkyl group comprising a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, and $R^5$ represents one or more linear, branched, or cyclic $C_3$~$C_7$ alkyl groups, $C_3$~$C_7$ aryl groups, $C_3$~$C_7$ heteroaryl groups or substituted heteroaryl groups, amino groups substituted with $C_3$~$C_7$ aryl alkyl groups or $C_3$~$C_7$ heteroaryl alkyl groups, thio groups or phenyl groups substituted with $C_3$~$C_7$ aryl alkyl groups or $C_3$~$C_7$ heteroaryl alkyl groups, substituted phenyl groups, benzyl groups, substituted benzyl groups, linear, branched, or cyclic $C_3$~$C_7$ alkyl groups, or amines with piperazine

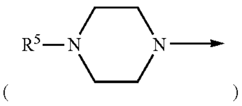

substituted with phenyl, heteroarylamide groups, wherein, in the $R^1$, $R^2$, $R^3$, and $R^4$, the substituted phenyl group, the substituted benzyl group, or the substituted $C_3$~$C_7$ heteroaryl group represents 1 to 3 substitutions of any one substituent selected from the group consisting of halogen atoms, nitro groups, $C_1$~$C_7$ alkyl groups, $C_1$~$C_7$ alkoxy groups, $C_1$~$C_7$ haloalkyl groups, and $C_1$~$C_7$ haloalkoxy groups.

3. The polysubstituted imidazolo[4,5-c][1,2]thiazine derivative and the pharmaceutically acceptable salt thereof, or the stereoisomer thereof of claim 1, wherein, in the Chemical Formula 1, $R^1$ is hydrogen, a linear, branched, or cyclic $C_3$~$C_7$ alkyl group; a phenyl group or $R^6$-substituted phenyl group; or a $R^6$-substituted or unsubstituted aromatic group, wherein the aromatic group represents a furanyl group, a thiophenyl group, a pyridinyl group, a pyridazinyl group, a quinolinyl group, or an isoquinolinyl group; and the $R^5$ is a 1 to 3 substituents selected from the group consisting of a hydrogen atom; a halogen atom; a hydroxy group; a cyano group; a nitro group; an amino group or amino group in which 1 to 2 linear, branched, or cyclic $C_3$~$C_5$ alkyl groups are substituted; a $C_1$~$C_5$ alkoxy group; and an alkoxy group comprising a substituted or unsubstituted aromatic ring, $R^2$ and $R^3$ are independently substituted hydrogen, a linear, branched, or cyclic $C_3$~$C_5$ alkyl group, a cyclic $C_3$~$C_5$ alkyl group comprising a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, $R^4$ is hydrogen, a linear, branched, or cyclic $C_3$ alkyl group, a cyclic $C_3$ alkyl group comprising a heteroatom (—NH—, —S—, —O—) or a heteroalkyl group, a phenyl group, a substituted phenyl group, an aryl group, a substituted aryl group, a benzyl group, a substituted benzyl group, a heteroaryl group, or a substituted heteroaryl group, and $R^5$ represents one or more linear, branched, or cyclic $C_3$~$C_7$ alkyl groups, $C_3$ aryl groups, $C_3$ heteroaryl groups or substituted heteroaryl groups, amino groups substituted with $C_3$ aryl alkyl groups or $C_3$ heteroaryl alkyl groups, thio groups or phenyl groups substituted with $C_3$ aryl alkyl groups or $C_3$ heteroaryl alkyl groups, substituted phenyl groups, benzyl groups, or substituted benzyl groups, wherein, in the $R^1$, $R^2$, $R^3$, and $R^4$, in the substituted phenyl groups, substituted benzyl groups, or substituted heteroaryl groups, the substituent represents 1 to 3 substitutions of any one substituent selected from the group consisting of $C_1$~$C_5$ alkyl groups, $C_1$~$C_5$ alkoxy groups, $C_1$~$C_5$ haloalkoxy groups, halogen groups, nitro groups, and amine groups.

4. The polysubstituted imidazolo[4,5-c][1,2]thiazine derivative and the pharmaceutically acceptable salt thereof, or the stereoisomer thereof of claim 1, wherein the polysubstituted imidazolo[4,5-c][1,2]thiazine derivative is one or more types selected from the group consisting of 1-benzyl-3,5-diphenyl-6-(propylthio)-3,5-dihydroimidazo[4,5-c][1,2]thiazine-4(1H)-one 2,2-dioxide, 1-benzyl-6-(benzylamino)-3,5-diphenyl-3,5-dihydroimidazo[4,5-c][1,2]thiazine-4(1H)-one 2,2-dioxide, 1-benzyl-6-(methylthio)-5-phenyl-3,5-dihydroimidazo[4,5-c][1,2]thiazine-4(1H)-one 2,2-dioxide, 1-benzyl-5-phenyl-6-(propylthio)-3,5-dihydroimidazo[4,5-c][1,2]thiazine-4(1H)-one 2,2-dioxide, 1-benzyl-6-(butylamino)-3,5-diphenyl-3,5-dihydroimidazo[4,5-c][1,2]thiazine-4(1H)-one 2,2-dioxide, 1-benzyl-6-(butylamino)-5-phenyl-3,5-dihydroimidazo[4,5-c][1,2]thiazine-4(1H)-one 2,2-dioxide, 1-ethyl-6-(methylsulfonyl)-3,5-diphenyl-3,5-dihydroimidazo[4,5-c][1,2]thiazine-1-benzyl-3-ethyl-6-(methylthio)-5-phenyl-3,5-dihydroimidazo[4,5-1-benzyl-6-(methylthio)-3,5-diphenyl-3,5-c][1,2]thiazine-4(1H)-one 2,2-dioxide, 4(1H)-one 2,2-dioxide, dihydroimidazo[4,5-c][1,2]thiazine-4(1H)-one 2,2-dioxide, 1-benzyl-6-(methylsulfonyl)-3,5-diphenyl-3,5-dihydroimidazo[4,5-c][1,2]thiazine-4(1H)-one 2,2-dioxide, 1-ethyl-3,5-diphenyl-6-(phenylthio)-3,5-dihydroimidazo[4,5-c][1,2]thiazine-4(1H)-one 2,2-dioxide, 1-ethyl-3,5-diphenyl-6-(propylthio)-3,5-dihydroimidazo[4,5-c][1,2]thiazine-4(1H)-one 2,2-dioxide, 6-(butylamino)-1-ethyl-3,5-diphenyl-3,5-dihydroimidazo[4,5-c][1,2]thiazine-4(1H)-one 2,2-dioxide, 6-(benzylamino)-1-ethyl-3,5-diphenyl-3,5-dihydroimidazo[4,5-c][1,2]thiazine-4(1H)-one 2,2-dioxide, 1-benzyl-3,5-diphenyl-6-(phenylthio)-3,5-dihydroimidazo[4,5-c][1,2]thiazine-4(1H)-one 2,2-dioxide, 1-benzyl-3-(4-chlorophenyl)-5-phenyl-6-(propylthio)-3,5-dihydroimidazo[4,5-c][1,2]thiazine-4(1H)-one 2,2-dioxide, 1-benzyl-3-(4-chlorophenyl)-5-phenyl-6-(phenylthio)-3,5-dihydroimidazo[4,5-c][1,2]thiazine-4(1H)-one 2,2-dioxide, 1-benzyl-6-(butylamino)-3-(4-chlorophenyl)-5-phenyl-3,5-dihydroimidazo[4,5-c][1,2]thiazine-4(1H)-one 2,2-dioxide, 1-benzyl-6-(benzylamino)-3-(4-chlorophenyl)-5-phenyl-3,5-dihydroimidazo[4,5-c][1,2]thiazine-4(1H)-one 2,2-dioxide, 3-(4-chlorophenyl)-1-ethyl-5-phenyl-6-(propylthio)-3,5-dihydroimidazo[4,5-c][1,2]thiazine-4(1H)-one 2,2-dioxide, 3-(4-chlorophenyl)-1-ethyl-5-phenyl-6-(phenylthio)-3,5-dihydroimidazo[4,5-c][1,2]thiazine-4(1H)-one 2,2-dioxide, 6-(butylamino)-3-(4-chlorophenyl)-1-ethyl-5-phenyl-3,5-dihydroimidazo[4,5-c][1,2]thiazine-4(1H)-one 2,2-dioxide, 6-(benzylamino)-3-(4-chlorophenyl)-

1-ethyl-5-phenyl-3,5-dihydroimidazo[4,5-c][1,2]thiazine-4(1H)-one 2,2-dioxide, 1-benzyl-3-(4-chlorophenyl)-3-methyl-5-phenyl-6-(propylthio)-3,5-dihydroimidazo[4,5-c][1,2]thiazine-4(1H)-one 2,2-dioxide, 1-benzyl-5-methyl-3-phenyl-6-(propylthio)-3,5-dihydroimidazo[4,5-c][1,2]thiazine-4(1H)-one 2,2-dioxide, 1-benzyl-5-methyl-3-phenyl-6-(phenylthio)-3,5-dihydroimidazo[4,5-c][1,2]thiazine-4(1H)-one 2,2-dioxide, 1-benzyl-6-(butylamino)-5-methyl-3-phenyl-3,5-dihydroimidazo[4,5-c][1,2]thiazine-4(1H)-one 2,2-dioxide, 1-benzyl-6-(butylamino)-5-methyl-3-phenyl-3,5-dihydroimidazo[4,5-c][1,2]thiazine-4(1H)-one 2,2-dioxide, 1-ethyl-5-methyl-3-phenyl-6-(propylthio)-3,5-dihydroimidazo[4,5-c][1,2]thiazine-4(1H)-one 2,2-dioxide, 1-ethyl-5-methyl-3-phenyl-6-(phenylthio)-3,5-dihydroimidazo[4,5-c][1,2]thiazine-4(1H)-one 2,2-dioxide, 6-(butylamino)-1-ethyl-5-methyl-3-phenyl-3,5-dihydroimidazo[4,5-c][1,2]thiazine-4(1H)-one 2,2-dioxide, 6-(benzylamino)-1-ethyl-5-methyl-3-phenyl-3,5-dihydroimidazo[4,5-c][1,2]thiazine-4(1H)-one 2,2-dioxide, 1-benzyl-3-(4-chlorophenyl)-5-methyl-6-(propylthio)-3,5-dihydroimidazo[4,5-c][1,2]thiazine-4(1H)-one 2,2-dioxide, 1-benzyl-3-(4-chlorophenyl)-5-methyl-6-(phenylthio)-3,5-dihydroimidazo[4,5-c][1,2]thiazine-4(1H)-one 2,2-dioxide, 1-benzyl-6-(butylamino)-3-(4-chlorophenyl)-5-methyl-3,5-dihydroimidazo[4,5-c][1,2]thiazine-4(1H)-one 2,2-dioxide, 1-benzyl-6-(benzylamino)-3-(4-chlorophenyl)-5-methyl-3,5-dihydroimidazo[4,5-c][1,2]thiazine-4(1H)-one 2,2-dioxide, 3-(4-chlorophenyl)-1-ethyl-5-methyl-6-(propylthio)-3,5-dihydroimidazo[4,5-c][1,2]thiazine-4(1H)-one 2,2-dioxide, 3-(4-chlorophenyl)-1-ethyl-5-methyl-6-(phenylthio)-3,5-dihydroimidazo[4,5-c][1,2]thiazine-4(1H)-one 2,2-dioxide, 6-(butylamino)-3-(4-chlorophenyl)-1-ethyl-5-methyl-3,5-dihydroimidazo[4,5-c][1,2]thiazine-4(1H)-one 2,2-dioxide, 6-(benzylamino)-3-(4-chlorophenyl)-1-ethyl-5-methyl-3,5-dihydroimidazo[4,5-c][1,2]thiazine-4(1H)-one 2,2-dioxide, 1-benzyl-3-(4-chlorophenyl)-5-methyl-6-(pyrrolidin-1-yl)-3,5-dihydroimidazo[4,5-c][1,2]thiazine-4(1H)-one 2,2-dioxide, 3-(4-chlorophenyl)-1-ethyl-5-methyl-6-(pyrrolidin-1-yl)-3,5-dihydroimidazo[4,5-c][1,2]thiazine-4(1H)-one 2,2-dioxide, 1-benzyl-6-morpholino-3,5-diphenyl-3,5-dihydroimidazo[4,5-c][1,2]thiazine-4(1H)-one 2,2-dioxide, 1-ethyl-3,3-dimethyl-6-(methylthio)-5-phenyl-3,5-dihydroimidazo[4,5-c][1,2]thiazine-4(1H)-one 2,2-dioxide, 1-ethyl-3-methyl-6-(methylthio)-5-phenyl-3,5-dihydroimidazo[4,5-c][1,2]thiazine-4(1H)-one 2,2-dioxide, 1,3-dibenzyl-6-(methylthio)-5-phenyl-3,5-dihydroimidazo[4,5-c][1,2]thiazine-4(1H)-one 2,2-dioxide, 1-benzyl-3-(4-methoxybenzyl)-6-(methylthio)-3,5-diphenyl-3,5-dihydroimidazo[4,5-c][1,2]thiazine-4(1H)-one 2,2-dioxide, 1-benzyl-5-methyl-3-phenyl-6-(phenylthio)-3,5-dihydroimidazo[4,5-c][1,2]thiazine-4(1H)-one 2,2-dioxide, 1-benzyl-6-(benzylamino)-5-methyl-3-phenyl-3,5-dihydroimidazo[4,5-c][1,2]thiazine-4(1H)-one 2,2-dioxide, 1,5-dimethyl-3-phenyl-6-(propylthio)-3,5-dihydroimidazo[4,5-c][1,2]thiazine-4(1H)-one 2,2-dioxide, 1,5-dimethyl-3-phenyl-6-(phenylthio)-3,5-dihydroimidazo[4,5-c][1,2]thiazine-4(1H)-one 2,2-dioxide, 6-(benzylamino)-1,5-dimethyl-3-phenyl-3,5-dihydroimidazo[4,5-c][1,2]thiazine-4(1H)-one 2,2-dioxide, 1-benzyl-5-methyl-6-(methylthio)-3-phenyl-3,5-dihydroimidazo[4,5-c][1,2]thiazine-4(1H)-one 2,2-dioxide, and 1,5-dimethyl-6-(methylsulfonyl)-3-phenyl-3,5-dihydroimidazo[4,5-c][1,2]thiazine-4(1H)-one 2,2-dioxide.

5. A pharmaceutical composition for preventing or treating an HMGB1 protein activation disease, comprising the polysubstituted imidazolo[4,5-c][1,2]thiazine derivative in claim 1 or a pharmaceutically acceptable salt thereof as an active ingredient.

6. The pharmaceutical composition of claim 5, wherein the HMGB1 protein activation disease is a vascular inflammatory disease or an infectious disease.

7. The pharmaceutical composition of claim 6, wherein the vascular inflammatory disease is any one selected from the group consisting of atherosclerosis, rheumatoid arthritis, aortic aneurysm, and diabetic peripheral vascular disease.

8. The pharmaceutical composition of claim 6, wherein the infectious disease is any one selected from the group consisting of inflammation, tuberculosis, sepsis, herpes, and hepatitis A, B and C accompanied by bacterial, viral or fungal infection.

* * * * *